US010385302B2

(12) United States Patent
Minamino et al.

(10) Patent No.: US 10,385,302 B2
(45) Date of Patent: Aug. 20, 2019

(54) DEVICE THAT PRODUCES SUGAR SOLUTION AND METHOD OF PRODUCING SUGAR SOLUTION

(71) Applicant: Toray Industries, Inc., Tokyo (JP)

(72) Inventors: Atsushi Minamino, Kamakura (JP);
Jumpei Kishimoto, Kamakura (JP);
Hiroyuki Kurihara, Kamakura (JP);
Katsushige Yamada, Kamakura (JP)

(73) Assignee: Toray Industries, Inc, Tokyo (JP)

( * ) Notice: Subject to any disclaimer, the term of this patent is extended or adjusted under 35 U.S.C. 154(b) by 789 days.

(21) Appl. No.: 14/759,513

(22) PCT Filed: Jan. 6, 2014

(86) PCT No.: PCT/JP2014/050037
§ 371 (c)(1),
(2) Date: Jul. 7, 2015

(87) PCT Pub. No.: WO2014/106953
PCT Pub. Date: Jul. 10, 2014

(65) Prior Publication Data
US 2015/0353881 A1  Dec. 10, 2015

(30) Foreign Application Priority Data

Jan. 7, 2013 (JP) .................................. 2013-000635

(51) Int. Cl.
*C12M 1/00* (2006.01)
*C12M 1/02* (2006.01)
(Continued)

(52) U.S. Cl.
CPC ............ *C12M 27/06* (2013.01); *C12M 23/58* (2013.01); *C12M 27/02* (2013.01); *C12M 29/00* (2013.01);
(Continued)

(58) Field of Classification Search
CPC ...... C12M 27/06; C12M 23/58; C12M 27/02; C12M 29/00; C12M 29/04; C12M 35/08;
(Continued)

(56) References Cited

U.S. PATENT DOCUMENTS 3,310,293 A * 3/1967 Zimmerman ......... B28C 9/0463
366/6
4,702,271 A * 10/1987 Giehl ...................... E03F 5/107
137/389
(Continued)

FOREIGN PATENT DOCUMENTS

CN  101177693  5/2008
CN  101998996  3/2011
(Continued)

OTHER PUBLICATIONS

The Second Office Action dated Nov. 3, 2016, of corresponding Chinese Application No. 20148003958.4, along with an English translation.
(Continued)

*Primary Examiner* — William H. Beisner
*Assistant Examiner* — Danielle B Henkel
(74) *Attorney, Agent, or Firm* — DLA Piper LLP (US)

(57) ABSTRACT

A device that produces a sugar solution from cellulose-containing biomass includes: a horizontal reaction tank that includes a stirring shaft provided along a horizontal direction in the horizontal reaction tank and a stirring blade provided to the stirring shaft, the horizontal reaction tank being configured to obtain a saccharified slurry by reacting the cellulose-containing biomass with a saccharification enzyme by stirring the cellulose-containing biomass and the saccharification enzyme; a vertical reaction tank configured to obtain a saccharified liquid by saccharifying the saccharified slurry; a saccharified slurry feed line that connects the
(Continued)

horizontal reaction tank and the vertical reaction tank; and a warming part provided around the horizontal reaction tank or on a wall surface of the horizontal reaction tank and heats the horizontal reaction tank.

15 Claims, 9 Drawing Sheets

(51) Int. Cl.
*C12M 1/06* (2006.01)
*C12M 1/42* (2006.01)
*C12P 19/02* (2006.01)
*C12P 19/14* (2006.01)
*C13K 1/02* (2006.01)

(52) U.S. Cl.
CPC ............ *C12M 29/04* (2013.01); *C12M 35/08* (2013.01); *C12M 41/14* (2013.01); *C12M 41/24* (2013.01); *C12P 19/02* (2013.01); *C12P 19/14* (2013.01); *C13K 1/02* (2013.01)

(58) Field of Classification Search
CPC ........ C12M 41/14; C12M 41/24; C12P 19/02; C12P 19/14; C13K 1/02
See application file for complete search history.

(56) References Cited

U.S. PATENT DOCUMENTS

| | | | | |
|---|---|---|---|---|
| 5,887,613 | A * | 3/1999 | Steinhardt | G05D 7/0106 137/395 |
| 6,375,345 | B1 | 4/2002 | Lepez et al. | |
| 2006/0157114 | A1* | 7/2006 | Stiehl | E03F 5/107 137/395 |
| 2007/0029252 | A1 | 2/2007 | Dunson, Jr. et al. | |
| 2007/0031918 | A1 | 2/2007 | Dunson, Jr. et al. | |
| 2007/0031919 | A1 | 2/2007 | Dunson, Jr. et al. | |
| 2007/0031953 | A1 | 2/2007 | Dunson, Jr. et al. | |
| 2007/0037259 | A1 | 2/2007 | Hennessey et al. | |
| 2008/0044877 | A1 | 2/2008 | Penttila et al. | |
| 2009/0053777 | A1 | 2/2009 | Hennessey et al. | |
| 2009/0098616 | A1 | 4/2009 | Burke et al. | |
| 2010/0178677 | A1 | 7/2010 | Dunson, Jr. et al. | |
| 2010/0248353 | A1* | 9/2010 | Lopez Zavala | B09B 3/00 435/290.2 |
| 2010/0285574 | A1 | 11/2010 | Genta et al. | |
| 2012/0009626 | A1 | 1/2012 | Suzuki et al. | |
| 2012/0107920 | A1 | 5/2012 | Taneda et al. | |
| 2012/0108673 | A1 | 5/2012 | Sethuraman et al. | |
| 2012/0125549 | A1 | 5/2012 | Romero et al. | |
| 2013/0004997 | A1 | 1/2013 | Mitsuzawa | |
| 2014/0113334 | A1 | 4/2014 | Romero et al. | |

FOREIGN PATENT DOCUMENTS

| | | |
|---|---|---|
| CN | 102112619 | 6/2011 |
| CN | 102859066 | 1/2013 |
| DE | 1 551 441 | 4/1971 |
| DE | 692 09 286 | 9/1996 |
| DE | 699 09 245 | 4/2004 |
| GB | 1158191 | 7/1969 |
| JP | 59-224694 | 12/1984 |
| JP | 05-317074 | 12/1993 |
| JP | 07-204611 A | 8/1995 |
| JP | 2001-238690 A | 9/2001 |
| JP | 2002-101865 A | 4/2002 |
| JP | 2005-229821 | 9/2005 |
| JP | 2007-099542 A | 4/2007 |
| JP | 2008-501330 A | 1/2008 |
| JP | 2008-535523 A | 9/2008 |
| JP | 2009-183805 A | 8/2009 |
| JP | 2010-104282 | 5/2010 |
| JP | 2010-254687 A | 11/2010 |
| JP | 2010-536375 A | 12/2010 |
| JP | 2011-019483 A | 2/2011 |
| JP | 2011-041493 A | 3/2011 |
| JP | 4764527 B1 | 6/2011 |
| WO | 92/19372 | 11/1992 |
| WO | 2011/114914 A1 | 9/2011 |
| WO | 2011/115039 | 9/2011 |
| WO | 2012/068578 A1 | 5/2012 |

OTHER PUBLICATIONS

Notification of Reasons for Refusal dated Dec. 26, 2016, of corresponding Japanese Application No. 2013-000635, along with an English translation.
The Third Office Action dated May 15, 2017, of corresponding Chinese Application No. 201480003958.4, along with an English translation.
Supplementary European Search Report dated Aug. 10, 2016, of corresponding European Application No. 14735171.2.
Decision of Refusal dated Sep. 5, 2017, of corresponding Japanese Application No. 2013-000635, along with an English translation.

* cited by examiner

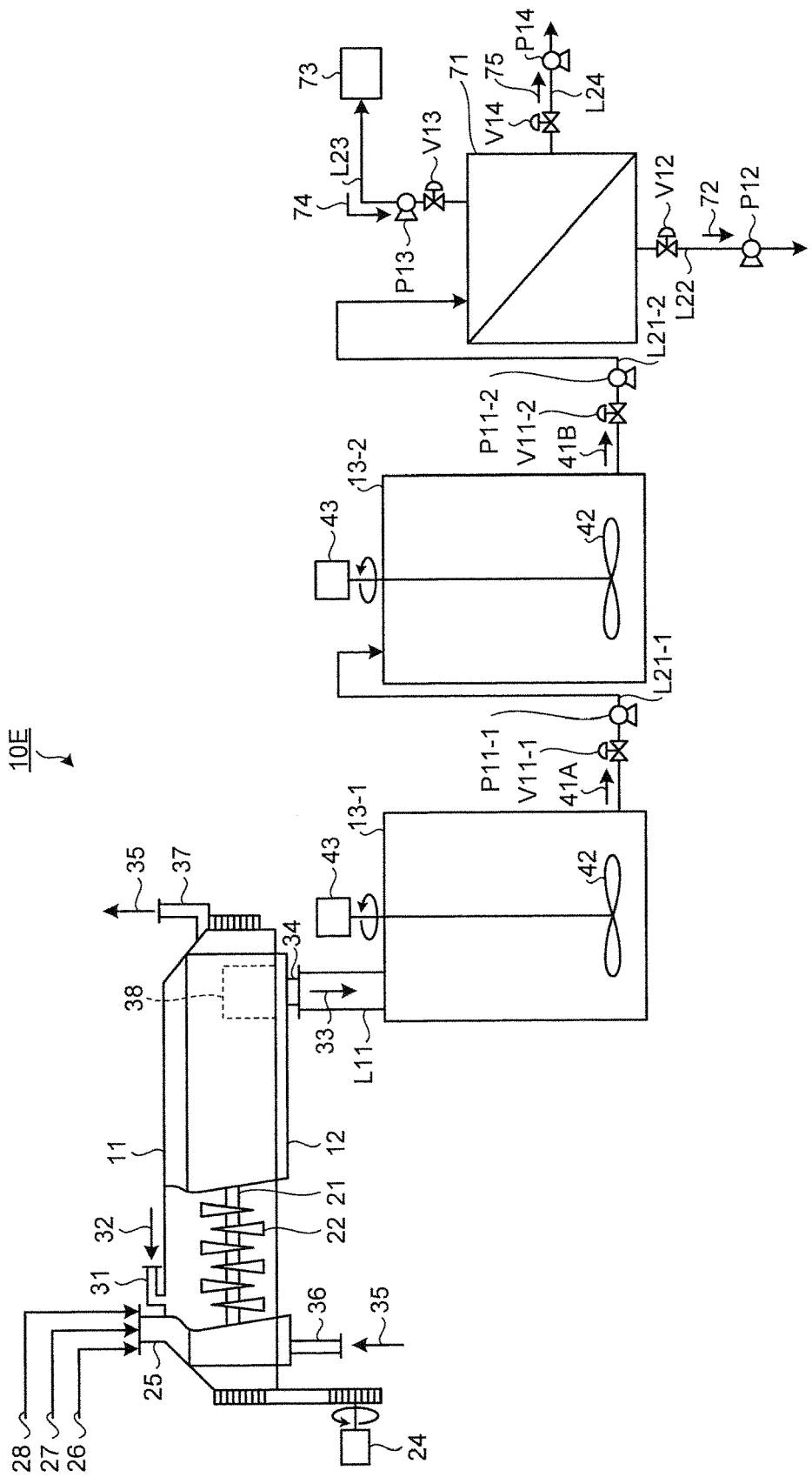

DEVICE THAT PRODUCES SUGAR SOLUTION AND METHOD OF PRODUCING SUGAR SOLUTION

TECHNICAL FIELD

This disclosure relates to a device that produces a sugar solution by yielding a sugar solution from cellulose-containing biomass and a method of producing a sugar solution.

BACKGROUND

A fermentation production process of chemicals using sugar as a raw material is used in various industrial raw material production. As the sugar to be a fermentation raw material, materials derived from food raw materials such as sugarcane, starch, and sugar beets are now industrially used. From the viewpoint of a steep increase in the price of the food raw materials due to an increase in future world population or ethical issue that the industrial raw material use competes against food use, establishment of a process in which a sugar solution is more efficiently produced from a reusable nonfood resource, that is, cellulose-containing biomass or a process in which the obtained sugar solution is efficiently converted into industrial raw materials as a fermentation raw material is a future problem.

The cellulose-containing biomass is mainly made of lignin that is an aromatic polymer and cellulose and hemicellulose that are polymers of monosaccharides. The sugar solution is generally obtained by using a method according to an enzymatic saccharification reaction. The method according to an enzymatic saccharification reaction, for example, includes the steps of carrying out pretreatment of lignin-protected cellulose or hemicellulose by mechanical treatment such as grinding treatment or thermochemical treatment using high temperature and high pressure water, dilutes sulfuric acid, and ammonia; removing cellulose or hemicellulose from lignin (refer to Japanese Patent Application Laid-open No. 2009-183805 and Japanese Translation of PCT Application No. 2008-535523) to obtain pretreated biomass; thereafter mixing a saccharification enzyme with the pretreated biomass; and hydrolyzing the cellulose or hemicellulose obtained by removal from the lignin with the saccharification enzyme to produce monosaccharides.

Production of the monosaccharides from the cellulose-containing biomass using the enzymatic saccharification reaction has a problem in facilities. First, efficiency of the saccharification derived from the cellulose-containing biomass using the saccharification enzyme (performance of the saccharification enzyme) is lower than that of the saccharification derived from starch and thus one day to several days are required for the hydrolysis reaction. Consequently, the residence time of the cellulose-containing biomass in the reaction equipment becomes longer and thus the facility cost becomes higher. Second, the saccharification reaction in high concentration of the cellulose-containing biomass may have such troubles that a stirrer does not rotate and a liquid (a slurry liquid) in a slurry state cannot be transferred. Consequently, the concentration of the cellulose-containing biomass at the time of enzymatic saccharification reaction has limitations and thus the concentration of the obtained sugar solution becomes low.

Various methods have been developed to solve the above problems in the facilities for the enzymatic saccharification reaction using the cellulose-containing biomass. Examples of the methods include a method of intermittently feeding pretreated biomass (for example, refer to Japanese Patent Application Laid-open No. 2001-238690 and Japanese Translation of PCT Application No. 2010-536375), a method of accelerating a reaction by once carrying out solid-liquid separation and mixing the residue and water (for example, refer to Japanese Patent Application Laid-open No. 2011-19483), a method of carrying out the saccharification reaction again after the grinding treatment of the residue (for example, refer to Japanese Patent Application Laid-open No. 2011-41493), and a method of adding water to pretreated biomass to form slurry (for example, refer to Japanese Patent No. 4764527).

However, although the method of intermittently feeding the pretreated biomass as described in JP '690 and JP '375 can increase sugar concentration at the time of saccharification, efficiency of the saccharification decreases because the reaction times of the saccharification enzyme of the pretreated biomasses fed in advance and the pretreated biomasses fed afterward are different.

The methods described in JP '483 and JP '493 suppress equilibrium reaction inhibition caused by the generated sugar to shorten the saccharification reaction time. However, the amount of added water is larger than the amount of water that is usually added. The method described in JP '493 requires additional energy to grind the material.

JP '527 discloses a method of reducing thermal overdecomposition of biomass by providing a slurrying tank. However, the liquid cannot be transferred without reducing the solid content concentration. As a result, the sugar concentration may decrease.

In the methods described above, problems remain in that the cellulose-containing biomass is difficult to saccharify in a high concentration or the facility cost becomes higher due to the longer reaction time.

In view of the above problems, it could be helpful to provide a device that produces a sugar solution that can effectively produce a sugar solution in a high concentration and a method of producing a sugar solution.

SUMMARY

We found that the saccharification reaction of the cellulose-containing biomass with the saccharification enzyme is improved and a high concentration sugar solution can be produced by providing a plurality of steps in a transferring direction of the cellulose-containing biomass in the reaction device and, at the same time, adjusting the temperature at the time of the saccharification reaction. The relation between the efficiency of the saccharification reaction and the sugar concentration of the sugar solution was clarified by firstly feeding the cellulose-containing biomass and the saccharification enzyme into a horizontal reaction tank, carrying out the saccharification reaction in two stages by mixing the saccharification enzyme with the cellulose-containing biomass while retaining the predetermined temperature in the tank and, thereafter, further carrying out the saccharification reaction in a vertical reaction tank to carry out the saccharification reaction. According to this obtained finding, the saccharification reaction is carried out in two stages of saccharifying the cellulose-containing biomass by the saccharification enzyme with transferring the cellulose-containing biomass in a horizontal direction to slurry the cellulose-containing biomass to form a slurry liquid and thereafter further progressing the saccharification reaction with transferring the slurry liquid in a vertical direction. By slurrying the cellulose-containing biomass in advance before the cellulose-containing biomass is transferred in the vertical direction, the reaction efficiency of the cellulose-containing biomass with the saccharification enzyme can be improved. The slurry has a low viscosity and thus the cellulose-containing biomass can be saccharified in a high concentration. As a result, we found that the cellulose-containing biomass can be efficiently reacted with the saccharification enzyme to further shorten the saccharification time and thus a high concentration sugar solution can be efficiently produced and in a low cost.

We thus provide:

(1) A device that produces a sugar solution from cellulose-containing biomass comprising:
  a horizontal reaction tank that includes a stirring shaft provided along a horizontal direction in the horizontal reaction tank and a stirring blade provided to the stirring shaft, the horizontal reaction tank being configured to obtain a saccharified slurry by reacting the cellulose-containing biomass with a saccharification enzyme by stirring the cellulose-containing biomass and the saccharification enzyme;
  a vertical reaction tank configured to obtain a saccharified liquid by saccharifying the saccharified slurry;
  a saccharified slurry feed line that connects the horizontal reaction tank and the vertical reaction tank; and
  a warming part that is provided around the horizontal reaction tank or on a wall surface of the horizontal reaction tank and heats the horizontal reaction tank.

(2) The device according to the above-described (1), wherein the horizontal reaction tank comprises:
  a biomass inlet that is located at one side of the horizontal reaction tank and feeds the cellulose-containing biomass; and
  a saccharified slurry outlet that is located at another side of the horizontal reaction tank opposite to the biomass inlet and discharges the saccharified slurry.

(3) The device for producing a sugar solution according to the above-described (1) or (2), wherein the horizontal reaction tank comprises a stemming part that is located at the saccharified slurry outlet and stems stream of the saccharified slurry.

(4) The device according to any one of the above-described (1) to (3), wherein the stirring shaft is heated.

(5) The device according to any one of the above-described (1) to (4), wherein at least one of the stirring shaft and the warming part is a hollow body through which a heat transfer medium is capable of flowing.

(6) The device according to the above-described (5), wherein a temperature of the heat transfer medium is 40° C. to 60° C.

(7) The device according to any one of the above-described (1) to (6), further comprising a biomass feed part that is located at a front stream side of the biomass inlet of the horizontal reaction tank and feeds the cellulose-containing biomass.

(8) The device according to any one of the above-described (1) to (7), further comprising:
  a saccharified liquid feed line that discharges the saccharified liquid from the vertical reaction tank; and
  a solid-liquid separation unit configured to obtain the sugar solution by separating a solid content from the saccharified liquid.

(9) The device according to the above-described (8), further comprising a warm water feed line that is connected to the solid-liquid separation unit and feeds warm water into the solid-liquid separation unit.

(10) The device according to any one of the above-described (1) to (9), wherein the horizontal reaction tank is provided with a plurality of such stirring shafts, and each of the stirring shafts is provided with a plurality of stirring blades.

(11) The device according to any one of the above-described (1) to (10), wherein the stirring blade has a cut-away part.

(12) The device according to any one of the above-described (1) to (11), wherein the vertical reaction tank comprises a second enzyme feed channel that feeds a saccharification enzyme into the vertical reaction tank.

(13) The device according to the above-described (12), wherein a saccharification enzyme fed into the horizontal reaction tank and a saccharification enzyme fed from the second enzyme feed channel are of different types.

(14) The device according to any one of the above-described (1) to (11), wherein a saccharification reaction of the cellulose-containing biomass with the saccharification enzyme in the horizontal reaction tank is carried out in an amount of dry mass of thermochemically treated cellulose-containing biomass of 15% by mass to 50% by mass relative to a whole mass of the saccharified slurry.

(15) The device according to the above-described (14), wherein the thermochemical treatment is selected from the group consisting of: ammonia treatment; hydrothermal treatment; blasting treatment; alkali treatment; and dilute sulfuric acid treatment.

(16) A method of producing a sugar solution from cellulose-containing biomass using the device for producing a sugar solution as claimed in any one of the above-described (1) to (15).

The cellulose-containing biomass is continuously saccharified with the saccharification enzyme to form the slurry with transferring the cellulose-containing biomass in the horizontal direction in the horizontal reaction tank while retaining the predetermined temperature in the horizontal reaction tank and whereby the low viscosity slurry liquid is formed in advance before the cellulose-containing biomass is transferred in the vertical direction. The saccharification reaction is further progressed with transferring the slurry liquid in the vertical direction in the vertical reaction tank and whereby the reaction efficiency of the cellulose-containing biomass with the saccharification enzyme can be improved and the cellulose-containing biomass can be saccharified in a high concentration. The high concentration sugar solution can be efficiently produced in a short period of time and in a low cost by carrying out the saccharification reaction in two stages of the horizontal reaction tank and the vertical reaction tank.

BRIEF DESCRIPTION OF THE DRAWINGS

FIG. 11 is a view illustrating another example of the configuration of the device that produces a sugar solution.

REFERENCE SIGNS LIST 10A to 10E Device for Producing Sugar Solution (Sugar Solution Production Device)
11 and 51 Horizontal reaction tank
11a Wall Surface
12 and 46 Jacket (Warming Part)
13 Vertical Reaction Tank
21, 21A, and 21B Stirring Shaft
22, 22A, 22B, and 42 Stirring Blade
22a Cut-away Part
24 Motor (Driving Unit)
25 Biomass Inlet
26 Cellulose-containing Biomass
27 Water
28 pH Adjuster
31 and 44 Enzyme Feed Channel
32 and 45 Saccharification Enzyme
33 Saccharified Slurry
33 Saccharified Slurry Outlet
35, 55, and 74 Warm Water
36 Warm Water Feed Channel for Jacket
37 Warm Water Discharge Channel for Jacket
38 Stemming Part
41 Saccharified Liquid
43 Vertical Stirring Driving Unit (Vertical Stirring Motor)
52 Hollow Stirring Shaft
53 Warm Water Feed Channel for Hollow Rotator
54 Warm Water Discharge Channel for Hollow Rotator
61 Biomass Feed Unit (Biomass Feed Part)
62 Hopper
63 Feeder Stirrer
64 Motor for Feeder Stirrer (Feeder Stirrer Driving Part)
65 Transfer Unit
66 Motor for Transfer Unit (Driving Part for Transfer Unit)
67 Solid Content Adjustment Water Feed Channel
71 Solid-Liquid Separation Unit
72 Sugar Solution
73 Warm Water Feed Tank
75 Saccharification Residue
L11 Saccharified Slurry Feed Line
L21, L21-1, and L21-2 Saccharified Liquid Feed Line
L22 Sugar Solution Discharge Line
L23 Warm Water Feed Line
L24 Saccharification Residue Discharge Line
P11 Saccharified Liquid Feed Pump
P12 Sugar Solution Feed Pump
P13 Warm Water Feed Pump
P14 Pump for Saccharification Residue Discharge
V11 to V14 Control Valve

DETAILED DESCRIPTION

Hereinafter, examples of our devices and methods will be described in detail with reference to the drawings. However, this disclosure is not limiting by the examples. The constituents in the following examples include constituents that those skilled in the art can easily assume, that are substantially the same, and that are what is called the range of equivalents. The constituents disclosed in the following examples may be appropriately combined or appropriately selected.

First Example

Device that Produces Sugar Solution

Figure 1:
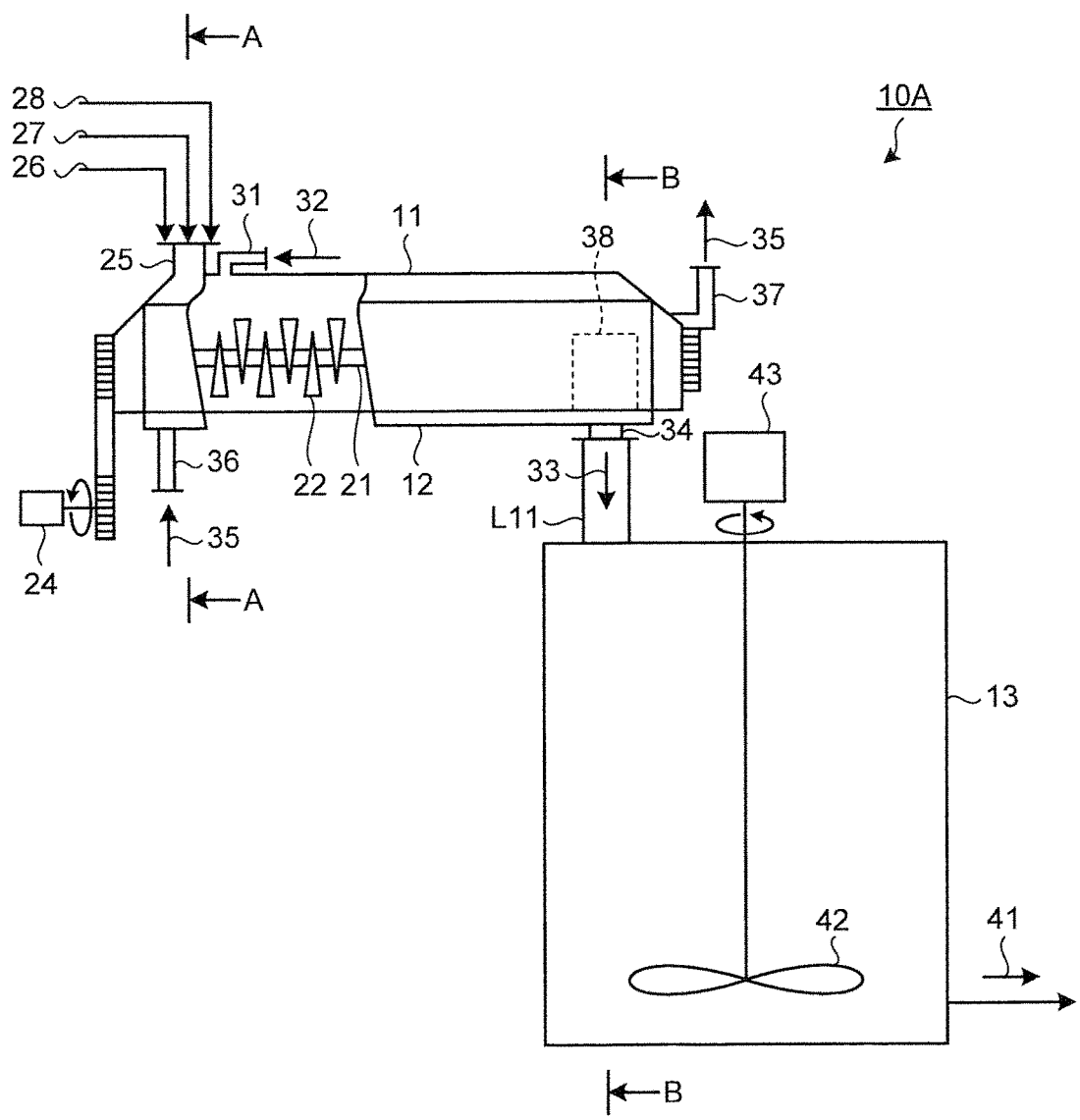
FIG. 1 is a partially cutout view of the device for producing a sugar solution according to a first example.
Figure 2:
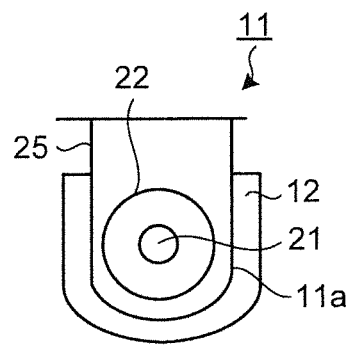
FIG. 2 is a sectional view of FIG. 1 taken along line A-A.
Figure 3:
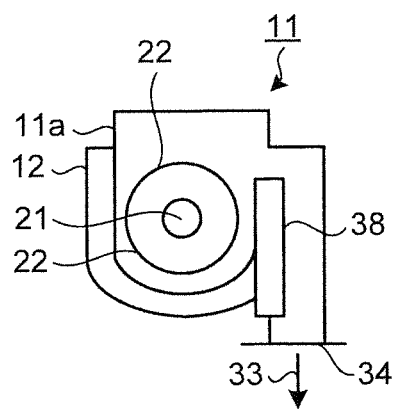
FIG. 3 is a sectional view of FIG. 1 taken along line B-B.

The device that produces a sugar solution (a sugar solution production device) according to a first examples will be described with reference to the drawings. FIG. 1 is a partial cutout view of the sugar solution production device according to the first example. FIG. 2 is a sectional view of FIG. 1 taken along line A-A. FIG. 3 is a sectional view of FIG. 1 taken along line B-B and a view illustrating a part of the configuration of the sugar solution production device. As illustrated in FIG. 1, the sugar solution production device 10A has a horizontal reaction tank (a transverse reaction tank) 11, a jacket (a warming part) 12, a vertical reaction tank (a longitudinal reaction tank) 13, and a saccharified slurry feed line L11.

The horizontal reaction tank 11 means a reaction tank in which a stirring shaft provided in the reaction tank is provided in a horizontal direction. The vertical reaction tank 13 means a reaction tank in which a stirring shaft provided in the reaction tank is provided along a vertical direction.

Horizontal Reaction Tank

As illustrated in FIG. 1 to FIG. 3, the horizontal reaction tank 11 includes a stirring shaft 21 and stirring blades 22.

The stirring shaft 21 is provided in the horizontal reaction tank 11 along the horizontal direction. The stirring blades 22 are provided on the stirring shaft 21 in given intervals. The stirring shaft 21 is rotated by a motor (a driving unit) 24 and stirs cellulose-containing biomass 26 fed into the horizontal reaction tank 11. The number of rotation of the stirring shaft 21 and the stirring blades 22 is controlled by the motor 24.

The horizontal reaction tank 11 is provided with a biomass inlet 25 located at one end side of the horizontal reaction tank 11. Cellulose-containing biomass 26, water 27, and a pH adjuster 28 are fed into the horizontal reaction tank 11 from the biomass inlet 25.

The biomass species of the cellulose-containing biomass 26 include cellulose and hemicellulose (hereinafter, cellulose and hemicellulose are referred to as "cellulose" as the collective term) and lignin being an aromatic polymer. The biomass species are not particularly limiting as long as the biomass species are resources of biologic origin containing 5% by mass or more of cellulose. The cellulose-containing biomass 26 contains lignin being an aromatic polymer and the like in addition to cellulose and thus is referred to as lignocellulose. The cellulose-containing biomass 26 is not particularly limiting as long as the biomass is a resource of biologic origin containing 5% by mass or more of cellulose. Specific examples of the biomass species include herbaceous biomass such as bagasse, switch grass, napier grass, erianthus, corn stover, rice straw, wheat straw, EFB (empty fruit bunche of oil palm), and rice husk and woody biomass such as woods and waste building materials. The cellulose-containing biomass 26 is mainly separated into a cellulose component, a hemicellulose component, a lignin component, and an inorganic component. Each component ratio is significantly different depending on the biomass species and growth conditions and thus is not particularly limiting.

Preferably, the cellulose-containing biomass 26 is pretreated before the cellulose-containing biomass 26 is fed into the horizontal reaction tank 11. The pretreatment of the cellulose-containing biomass 26 enables the efficiency of the hydrolysis by the saccharification enzyme to be improved. A method of pretreating the cellulose-containing biomass 26 is not particularly limiting and pretreatment methods that have been conventionally known can be used. Examples of the pretreatment method include thermochemical treatment such as hydrothermal treatment, ammonia treatment, alkali treatment, and dilute sulfuric acid treatment, pulverization treatment, blasting treatment, acid treatment, sulfuric acid treatment, sodium hydroxide treatment, subcritical water treatment, and steam treatment. Any one of these treatments may be used or these treatments can be used in combination.

The water 27 is not particularly limiting. Well water, industrial water, tap water, river water, process discharged water, and process regeneration water may be used or a mixture of these waters may be used.

As the pH adjuster 28, an acid or an alkali is preferably used from the viewpoint of economic efficiency. Whether the acid or the alkali is used as the additive depends on the pretreatment method. For example, the alkali agent is used in the hydrothermal treatment, the diluted sulfuric acid treatment, the blasting treatment, the acid treatment, the sulfuric acid treatment, the subcritical water treatment, the steam treatment or the like, whereas the acid is used in the case of the ammonia treatment, the alkali treatment or the like. Examples of the alkali may include sodium hydroxide, ammonia, and calcium hydroxide. Examples of the acid may include sulfuric acid, hydrochloric acid, phosphoric acid, and organic acids such as acetic acid. When a small amount of the organic acid and the like of the cellulose-containing biomass 26 origin in the pretreatment product is used, pH control is difficult. In this case, a buffering agent such as sodium acetate, sodium phosphate, sodium citrate may be added.

In the horizontal reaction tank 11, an enzyme feed channel 31 connects to the downstream side of the biomass inlet 25 in a flow direction of the cellulose-containing biomass 26. In the horizontal reaction tank 11, a saccharification enzyme 32 is fed into the horizontal reaction tank 11 from the enzyme feed channel 31. The reason why the enzyme feed channel 31 connects to the downstream side of the biomass inlet 25 is that the saccharification enzyme 32 may be deactivated and the saccharification reaction may fail to be progressed, particularly when the cellulose-containing biomass 26 whose pH is not adjusted is reacted with the saccharification enzyme 32. When pH of the cellulose-containing biomass 26 is adjusted 4 or more and 6 or less, the enzyme feed channel 31 does not have to be provided in the horizontal reaction tank 11. In this case, the saccharification enzyme 32 may be fed from the biomass inlet 25.

The saccharification enzyme 32 means an enzyme component that has activity to decompose cellulose or hemicellulose or assists the decomposition of cellulose or hemicellulose. Specific examples of the enzyme component may include cellobiohydrolase, endoglucanase, exoglucanase, β-glucosidase, xylanase, xylosidase, and a biomass swelling enzyme. As the saccharification enzyme 32, these enzyme components may be used singly or in combination of them. The hydrolysis of cellulose and hemicellulose can be efficiently carried out by the concerted effect or the complementary effect of a plurality of enzyme components and thus the saccharification enzyme 32 is preferably an enzyme mixture containing the above enzyme components.

As the saccharification enzyme 32, a saccharification enzyme produced by microorganisms may also be preferably used. For example, the saccharification enzyme 32 may be a saccharification enzyme that contains a plurality of enzyme components produced by one species of microorganism or may be a saccharification enzyme that contains the mixture of enzyme components produced by a plurality of microorganisms. The microorganism producing the saccharification enzyme 32 is microorganism that intracellularly or extracellularly produces the saccharification enzyme and is preferably a microorganism that extracellularly produces the saccharification enzyme. This is because the saccharification enzyme is more easily recovered from the microorganism that extracellularly produces the saccharification enzyme.

The microorganism that produces the saccharification enzyme 32 is not particularly limiting as long as the microorganism produces the enzyme components. Particularly, filamentous fungi classified as *Trichoderma* and *Acremonium* extracellularly secrete large amounts of various saccharification enzymes and thus they may be particularly suitably used as the microorganisms producing the saccharification enzyme 32.

The saccharification enzyme 32 may be an unused saccharification enzyme. Alternatively, the saccharification enzyme recovered in a solid-liquid separation unit 71 described below may be reused. From the viewpoint of the used amount of the saccharification enzyme 32, particularly, reduction in the amount used of an unused saccharification enzyme, a mixture of both of the recovered saccharification enzyme and the unused saccharification enzyme is preferably used.

Although a method of feeding the cellulose-containing biomass 26, the water 27, the pH adjuster 28, and the saccharification enzyme 32 is not particularly limiting, it is preferable that these materials are quantitatively and continuously fed with the pump.

The cellulose-containing biomass 26, the water 27, the pH adjuster 28, and the saccharification enzyme 32 are mixed and reacted in the horizontal reaction tank 11 to generate saccharified slurry 33 in a slurry state.

In the horizontal reaction tank 11, a saccharified slurry outlet 34 is provided at the side opposite to the biomass inlet 25 and in the downstream side in the flow direction of the cellulose-containing biomass 26 in the horizontal reaction tank 11. In the horizontal reaction tank 11, the cellulose-containing biomass 26 and the saccharification enzyme 32 are reacted to generate the saccharified slurry 33 by stirring the cellulose-containing biomass 26 and the saccharification enzyme 32. The saccharified slurry 33 is discharged from the horizontal reaction tank 11 through the saccharified slurry outlet 34.

Jacket

A jacket 12 is provided at the wall surface 11a of the horizontal reaction tank 11. The jacket 12 warms the inside of the horizontal reaction tank 11 from the outside. The jacket 12 is a hollow body through which warm water (a heat transfer medium) can flow. The jacket 12 is provided at the wall surface 11a.

Although the jacket 12 is defined as a hollow body through which warm water can flow, the jacket is not limited to this configuration. The jacket 12 may be a jacket that can heat the horizontal reaction tank 11 from the outside, for example, a jacket providing a heating source such as an electric heater therein and a jacket into which steam is fed in an extremely low amount or intermittently.

The jacket 12 is provided at the wall surface 11a. However, the example is not limited to this configuration. The jacket 12 may be a jacket that warms the horizontal reaction tank 11 from the outside and may be provided to cover the whole horizontal reaction tank 11.

The jacket 12 is used to warm the horizontal reaction tank 11. However, the example is not limited to this configuration. The warming method is not particularly limiting and may be any appropriate method that can warm the horizontal reaction tank 11 such as a method of winding a water pipe or a rod heater around the outer circumference of the horizontal reaction tank 11.

Warming the inside of the horizontal reaction tank 11 at the time of saccharifying the cellulose-containing biomass 26 enables a sequence of saccharification reaction time for obtaining a saccharified liquid 41 to be shortened. Particularly, warming the jacket 12 and the stirring shaft 21 enables the saccharification reaction time to be shortened and, at the same time, the viscosity of the saccharified slurry 33 to be reduced.

The temperature in the horizontal reaction tank 11 is controlled by the jacket 12. Warm water 35 is fed into a warm water discharge channel for jacket 37 from a warm water feed channel for jacket 36 passing through the inside of the jacket 12. A temperature and a warm water feed rate of the warm water 35 can be set, and they are appropriately adjusted depending on the temperature in the horizontal reaction tank 11. So that the saccharification enzyme 32 works effectively, the temperature in the horizontal reaction tank 11 is preferably 37° C. or more, more preferably 40° C. or more and 60° C. or less, and further preferably 45° C. or more and 55° C. or less. This is because the temperature in the horizontal reaction tank 11 of 40° C. or more is an optimum temperature for the saccharification enzyme 32 and results in difficulty in proliferation of bacteria such as molds that proliferate with sugar. This is also because the temperature in the horizontal reaction tank 11 of more than 60° C. causes deactivation of the saccharification enzyme 32. The temperature in the horizontal reaction tank 11 is controlled by the jacket 12. However, this example is not limited to this configuration. The control of the temperature may be carried out by any appropriate method of warming the horizontal reaction tank 11 from the outside.

A reaction time of the cellulose-containing biomass 26 with the saccharification enzyme 32 in the horizontal reaction tank 11 is preferably 5 minutes to 4 hours and more preferably 10 minutes to 1 hour. This is because the reaction time of less than 5 minutes results in insufficient saccharification and insufficient reduction in the viscosity and this may cause troubles in liquid transfer and stirring of the saccharified slurry 33 discharged from the saccharified slurry outlet 34. On the other hand, the reaction time of more than 4 hours results in separation of the discharged saccharified slurry 33 into the solid product and the liquid product. This may cause difficulty in continuous discharge of the saccharified slurry 33 because the main component of the discharged substance is the liquid component and only the solid product of the saccharified slurry 33 remains. The reaction time in the horizontal reaction tank 11 is controlled by the feed rate of the cellulose-containing biomass 26, the number of rotation of a stemming part 38, the stirring shaft 21, and the stirring blade 22, and the like.

The mixing order of the cellulose-containing biomass 26, the water 27, the pH adjuster 28, and the saccharification enzyme 32 is not particularly limiting. Examples of the mixing methods are as follows. Examples of the methods include a method of mixing the cellulose-containing biomass 26 with the pH adjuster 28, and thereafter mixing the water 27 and mixing the saccharification enzyme 32; a method of mixing the cellulose-containing biomass 26 with the water 27, and thereafter mixing the pH adjuster 28 with the saccharification enzyme 32 in this order; a method of mixing the solution of the pH adjuster 28 diluted with the water 27 with the solution of the cellulose-containing biomass 26, and thereafter mixing the saccharification enzyme 32; and a method of simultaneously mixing the cellulose-containing biomass 26, the pH adjuster 28, the water 27, and the saccharification enzyme 32. The method of mixing the cellulose-containing biomass 26 and the pH adjuster 28, and thereafter mixing the water 27 and mixing the saccharification enzyme 32 is preferable. Specifically, the cellulose-containing biomass 26 and the pH adjuster 28 are fed into the horizontal reaction tank 11 and thereafter the water 27 is fed to the mixture of the cellulose-containing biomass 26 and the pH adjuster 28 to provide minimum flowability.

The cellulose-containing biomass 26, the pH adjuster 28, and the water 27 in the horizontal reaction tank 11 are stirred and mixed to prepare a mixed liquid of the cellulose-containing biomass 26, the pH adjuster 28, and the water 27. The pH of the mixed liquid is preferably 3 or more and 7 or less and more preferably 4 or more and 6 or less. The saccharification enzyme 32 can suitably work by controlling the pH of the mixed liquid within the above range. It is preferable that the constant pH is adjusted to be retained using an acid or an alkali, because change in the pH of the mixed liquid occurs during the hydrolysis of the mixed liquid.

Subsequently, after the pH of the mixed liquid is adjusted, the saccharification enzyme 32 is fed into the horizontal reaction tank 11 through the enzyme feed channel 31 and then the mixed liquid containing the cellulose-containing biomass 26, the water 27, and the pH adjuster 28 is reacted with the saccharification enzyme 32 to carry out the saccharification reaction. This gives the hydrolysis product of the cellulose-containing biomass 26. The hydrolysis product is the saccharified liquid 41 containing a sugar solution 72 and a solid content described later. Addition of the water 27 into the horizontal reaction tank 11 is not always required, depending on the stirring conditions of the cellulose-containing biomass 26 in the horizontal reaction tank 11.

The cellulose-containing biomass 26 is discharged as a reactant containing the pH adjuster 28, the water 27, and the saccharification enzyme 32 from the saccharified slurry outlet 34 as the saccharified slurry 33. To continuously discharge the saccharified slurry 33 from the saccharified slurry outlet 34, the number of rotation of the stirring shaft 21 and the stirring blades 22 is adjusted by the motor 24. This prevents generation of a retention part of the cellulose-containing biomass 26 in the horizontal reaction tank 11, thereby suppressing the rapid lowering of the viscosity of the saccharified slurry 33 caused by the reaction of the mixed slurry of the cellulose-containing biomass 26, the water 27, and the pH adjuster 28 with the saccharification enzyme 32.

The dried amount of the cellulose-containing biomass 26 to which thermochemical treatment is applied is preferably 15% by mass or more and 50% by mass or less relative to the whole mass of the saccharified slurry 33 when the saccharification reaction of the cellulose-containing biomass 26 with the saccharification enzyme 32 is carried out. This is because the dried amount of the cellulose-containing biomass 26 to which thermochemical treatment is applied of more than 50% prevents slurry formation even using the horizontal reaction tank 11 and prevents the progress of the saccharification reaction. Examples of the thermochemical treatment may include ammonia treatment, hydrothermal treatment, blasting treatment, alkali treatment, and dilute sulfuric acid treatment.

The horizontal reaction tank 11 is provided with the stemming part 38 at the saccharified slurry outlet 34. The stemming part 38 is a plate-like member provided so that the saccharified slurry outlet 34 is surrounded by the stemming part 38 and the wall surface 11a of the horizontal reaction tank 11. The stemming part 38 stems the flow of the saccharified slurry 33. The stemming part 38 may be located near the saccharified slurry outlet 34. The stemming part 38 is provided in the same direction as the transfer direction of the saccharified slurry 33 in the horizontal reaction tank 11. However, example is not limited to this configuration. The stemming part 38 may be provided in a vertical direction of the horizontal reaction tank 11. The location position of the stemming part 38 is not particularly limiting.

The height of the stemming part 38 is adjusted so that continuous discharge of the saccharified slurry 33 does not become difficult due to the separation of the saccharified slurry 33 into the solid product and the liquid product when the saccharified slurry 33 is discharged from the saccharified slurry outlet 34. The saccharified slurry 33 can be continuously and stably discharged from the saccharified slurry outlet 34 by adjusting the height of the stemming part 38 to a height over which the saccharified slurry 33 can be continuously discharged.

The saccharified slurry feed line L11 connects the horizontal reaction tank 11 and the vertical reaction tank 13. The saccharified slurry 33 is fed into the vertical reaction tank 13 from the horizontal reaction tank 11 through the saccharified slurry feed line L11.

The horizontal reaction tank 11 is installed horizontally to an installation surface. The horizontal reaction tank 11, however, may be installed so that the horizontal reaction tank 11 is inclined downwards at a given angle (for example, 1° to 10°) in a direction of the saccharified slurry outlet 34. This can improve transfer efficiency of the cellulose-containing biomass 26.

Vertical Reaction Tank

The vertical reaction tank 13 is a tank in which the saccharified liquid 41 is generated by saccharifying the saccharified slurry 33. The vertical reaction tank 13 is provided with stirring blades 42 therein. The stirring blades 42 are driven by the vertical stirring driving unit (a vertical stirring motor) 43. The saccharified slurry 33 is stirred with the stirring blades 42 to continuously carry out the saccharification reaction in the vertical reaction tank 13. This converts the saccharified slurry 33 into the saccharified liquid 41.

The saccharified slurry 33 is stirred with transforming in the vertical reaction tank 13 from the top side to the bottom side. Consequently, the vertical reaction tank 13 can reduce operation power compared with the horizontal reaction tank 11 in which the saccharified slurry 33 is transferred with stirring and can reduce the operation power compared with the horizontal reaction tank 11 in which the saccharified slurry 33 is retained. This can reduce the facility cost. The saccharified slurry 33 has low viscosity and has good flowability. This eliminates the need for horizontal stirring in the horizontal reaction tank 11 and the saccharified slurry 33 is easily discharged at the time of liquid transfer to the next process.

The time of the saccharification reaction of the saccharified slurry 33 in the vertical reaction tank 13 is preferably 1 hour or more and 72 hours or less and more preferably 4 hours or more and 24 hours or less.

The saccharified liquid 41 is discharged from the bottom part of the vertical reaction tank 13. A method of discharging the saccharified liquid 41 is not particularly limiting and the saccharified liquid 41 may be continuously or intermittently discharged. For example, the vertical reaction tank 13 can be placed in multi stages to form a reaction form such as a CSTR (Continuous Stirred Tank Reactor) when the saccharified liquid 41 is continuously discharged. A method of discharging the saccharified liquid 41 in every batch in the reaction time as described above when the saccharified liquid 41 is intermittently discharged or a method of discharging the saccharified liquid 41 synchronized with the batch processing time of the solid-liquid separation unit when the solid-liquid separation unit is provided in the latter stage of the vertical reaction tank 13 is also exemplified. Consequently, a rate of forward transfer of the cellulose-containing biomass 26 in the vertical direction in the vertical reaction tank 13 may be extremely slow and may be intermittent in some cases.

As described above, the sugar solution production device 10A is provided with the horizontal reaction tank 11, the jacket 12, and the vertical reaction tank 13. The saccharified slurry 33 is generated by mixing the cellulose-containing biomass 26, the water 27, the pH adjuster 28, and the saccharification enzyme 32 in the horizontal reaction tank 11 and the saccharified liquid 41 is generated from the saccharified slurry 33 in the vertical reaction tank 13. In the sugar solution production device 10A, the saccharification reaction of the cellulose-containing biomass 26 is carried out in two stages using the horizontal reaction tank 11 and vertical reaction tank 13 and whereby the saccharified liquid 41 having a high concentration can be produced in a short period of time efficiently. The two-stage saccharification reaction enables the saccharification reaction to be carried out in the vertical reaction tank 13 in a high solid content concentration of the saccharified liquid 41 of 15% by mass or more. Consequently, the sugar solution production device 10A allows reduction in a saccharification rate associated with the saccharification reaction in a high concentration observed in a conventional vertical reaction tank to be prevented and the saccharification reaction to be carried out in a higher concentration. Therefore, the saccharification reaction can be progressed in a short period of time.

In other words, the saccharification reaction of the cellulose-containing biomass 26 carried out only in the vertical reaction tank 13 as the conventional method may fail to progress the enzyme reaction using only the vertical reaction tank 13 because the viscosity of the cellulose-containing biomass 26 or the saccharified slurry 33 may increase or cellulose-containing biomass 26 or the saccharified slurry 33 may solidify when the solid content concentration of the cellulose-containing biomass 26 is high. In this case, the load of the stirring blade 42 is increased. As a result, in the conventional method, the solid content concentration of the saccharified liquid 41 may have been raised to at most about 15% by mass and thus the saccharified liquid 41 having a high concentration has been difficult to be obtained. On the other hand, in the sugar solution production device 10A, the horizontal reaction tank 11 and the vertical reaction tank 13 are serially combined to the flow direction of the cellulose-containing biomass 26. First, the cellulose-containing biomass 26 is saccharified with the saccharification enzyme 32 to form slurry in the horizontal reaction tank 11 with transferring the cellulose-containing biomass 26 in the horizontal direction while the given temperature in the tank is retained. In this way, the saccharified slurry 33 having a low viscosity is formed in advance by forming the slurry before the cellulose-containing biomass 26 is transferred in the vertical direction. This can improve reaction efficiency at the time of the saccharification in the next vertical reaction tank 13. Thereafter, the saccharification reaction is further progressed in the vertical reaction tank 13 with transferring the saccharified slurry 33 in the vertical direction to carry out the two-stage saccharification reaction. The reaction efficiency of the cellulose-containing biomass 26 with the saccharification enzyme 32 can be improved by slurrying the cellulose-containing biomass 26 into the saccharified slurry 33 in advance before the saccharification reaction is progressed by transferring the cellulose-containing biomass 26 in the vertical direction. The saccharified slurry 33 has low viscosity and thus can be saccharified in a high concentration in the vertical reaction tank 13. As a result, the cellulose-containing biomass 26 is efficiently reacted with the saccharification enzyme 32 in the sugar solution production device 10A and thus the saccharified liquid 41 having a high concentration can be efficiently produced in a low cost.

Accordingly, in the sugar solution production device 10A, the saccharification reaction can be continuously carried out in a high concentration of the solid content concentration of the saccharified liquid 41 and in high efficiency compared with the conventional method of carrying out the saccharification reaction only in the vertical reaction tank and thus the saccharification efficiency of the saccharification reaction can be improved. Consequently, the condensation cost of the saccharified liquid 41 and a fermentation product can be reduced. In addition, a smaller sugar solution production device 10A can be made and the facility cost can be reduced by shortening the reaction time.

The horizontal reaction tank 11 is warmed by the jacket 12. However, the example is not limited to this configuration. For example, the stirring shaft 21 may be warmed by forming the stirring shaft 21 as a hollow body through which warm water can flow.

The horizontal reaction tank 11 has the stemming part 38. However, this example is not limited to this configuration. The horizontal reaction tank 11 does not necessarily have the stemming part 38 when the discharge of the saccharified slurry 33 is stable.

Figure 4:
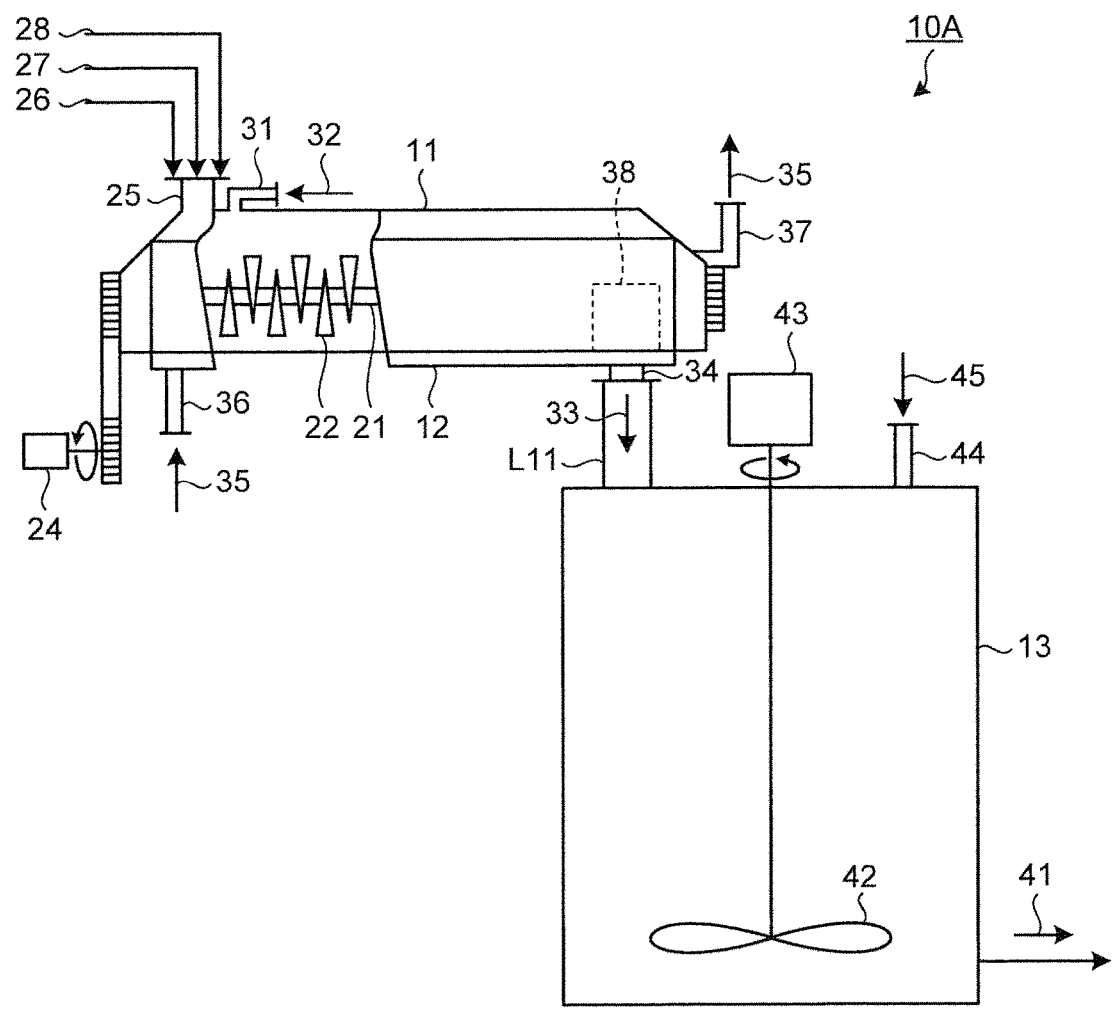
FIG. 4 is a view illustrating another configuration of the device that produces a sugar solution.

The saccharification enzyme 32 is fed only into the horizontal reaction tank 11. However, this example is not limited to this configuration. As illustrated in FIG. 4, the vertical reaction tank 13 may be provided with a second enzyme feed channel 44 and a saccharification enzyme 45 may be fed into the vertical reaction tank 13. The saccharification reaction of the saccharified slurry 33 formed in the horizontal reaction tank 11 can be further accelerated in the vertical reaction tank 13.

The types of the saccharification enzyme 32 and the saccharification enzyme 45 are preferably different from each other when the saccharification enzyme 32 is fed into the horizontal reaction tank 11 and the saccharification enzyme 45 is fed into the vertical reaction tank 13. In other words, in the initial stage of the saccharification reaction carrying out in the horizontal reaction tank 11, polysaccharides such as cellulose and hemicellulose are decomposed to oligosaccharides by the saccharification enzyme 32. In the vertical reaction tank 13, the oligosaccharides are decomposed to monosaccharides by the saccharification enzyme 45 to promote the saccharification reaction of the cellulose-containing biomass 26 contained in the saccharified slurry 33.

Figure 5:
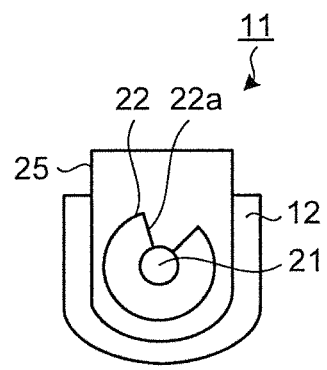
FIG. 5 is a view illustrating another example of the horizontal reaction tank of the device that produces a sugar solution.

The stirring blades 22 are provided around the whole surface of the stirring shaft 21 in the circumferential direction of the stirring shaft 21 in the horizontal reaction tank 11. However, this example is not limited to this configuration. The stirring blade 22 may have a cut-away part 22a that is a cut-away provided on a part of the stirring blade 22 positioned along the circumferential direction of the stirring shaft 21. One example of the cut-away part 22a provided in the stirring blade 22 is illustrated in FIG. 5. FIG. 5 is a sectional view of the horizontal reaction tank 11 seen from an axial direction. As illustrated in FIG. 5, the stirring blade 22 has the cut-away part 22a and whereby the cellulose-containing biomass 26 is stirred by the cut-away part 22a of the stirring blade 22. This allows the reaction efficiency with the saccharification enzyme 32 to be improved and, at the same time, the reaction to be carried out at the optimum temperature for the saccharification enzyme 32 through the stirring blade 22. One cut-away part 22a is provided in the stirring blade 22. However, this example is not limited to this configuration. The stirring blade 22 may have two or more cut-away parts 22a. The stirring blade 22 having the cut-away part 22a allows easy transfer of the cellulose-containing biomass 26 and the saccharification enzyme 32 toward the saccharified slurry outlet 34 with being pushed by the newly charged cellulose-containing biomass 26. Consequently, the cellulose-containing biomass 26 and the like can be continuously transferred to the saccharified slurry outlet 34 through the cut-away part 22a of the stirring blade 22.

Figure 6:
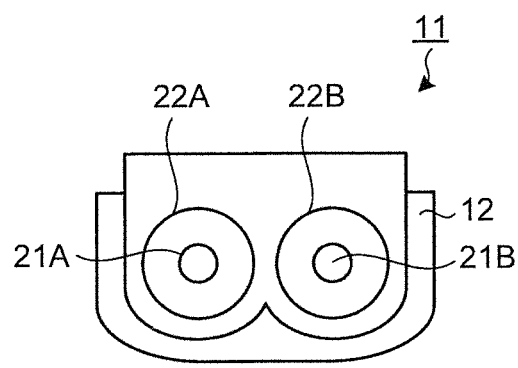
FIG. 6 is a view illustrating another example of the horizontal reaction tank of the device that produces a sugar solution.

The horizontal reaction tank 11 is provided with one stirring shaft 21. However, example is not limited to this configuration. The horizontal reaction tank 11 may be provided with a plurality of stirring shaft 21. On example of the horizontal reaction tank 11 provided with two stirring shafts 21 is illustrated in FIG. 6. FIG. 6 is a sectional view of the horizontal reaction tank 11 provided with two stirring shafts 21 seen from the axial direction. As illustrated in FIG. 6, the horizontal reaction tank 11 is provided with stirring shafts 21A and 21B along the horizontal direction with respect to the axial direction of the horizontal reaction tank 11. Each of the stirring shafts 21A and 21B is provided with a plurality of stirring blades 22A and 22B respectively on the stirring shafts 21A and 21B at given intervals. This enables the mixing efficiency of the cellulose-containing biomass 26, the water 27, the pH adjuster 28, and the saccharification enzyme 32 to be improved in the horizontal reaction tank 11 and thus enables the production efficiency of the saccharified slurry 33 to be improved.

Figure 7:
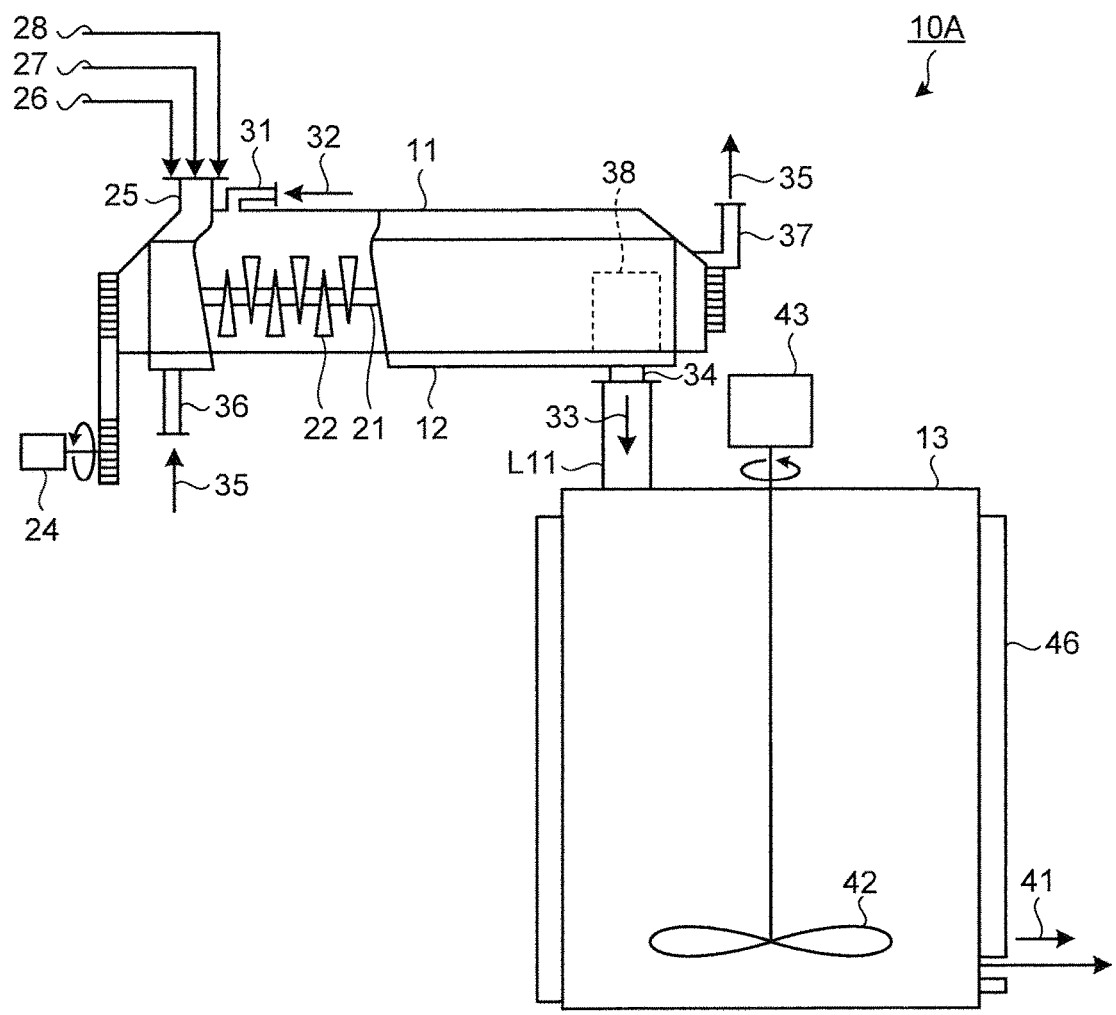
FIG. 7 is a view illustrating another example of the configuration of the vertical reaction tank of the device that produces a sugar solution.

No warming part is provided around the circumference of the vertical reaction tank 13. However, this example is not limited to this configuration. The vertical reaction tank 13 may be provided with the warming part around its circumference. Examples of the warming part may include a jacket that is provided so that the jacket covers the wall surface or the circumference of the vertical reaction tank 13. One example in which a jacket is provided at the wall surface of the vertical reaction tank 13 is illustrated in FIG. 7. FIG. 7 is a view illustrating another example of the configuration of the vertical reaction tank 13. As illustrated in FIG. 7, the vertical reaction tank 13 is provided with a jacket 46 at the wall surface. The jacket 46 is a hollow body through which warm water can flow. Similar to the jacket 12, warm water that flow through the jacket 46 is preferably 40° C. or more and 60° C. or less and more preferably 45° C. or more and 55° C. or less. This is because the temperature in the vertical reaction tank 13 of 40° C. or more is an optimum temperature for the saccharification enzyme 32 and results in difficulty in proliferation of bacteria such as molds that proliferate by sugar. This is also because a temperature of more than 60° C. in the vertical reaction tank 13 causes deactivation of the saccharification enzyme 32.

Second Example

The sugar solution production device according to a second example will be described with reference to the drawings. The configuration of the sugar solution production device according to this example is similar to the configuration of the sugar solution production device according to the first example as illustrated in FIG. 1 above and thus the same reference signs are assigned to the same members in the sugar solution production device according to the first example and the description of the same members is omitted.

Figure 8:
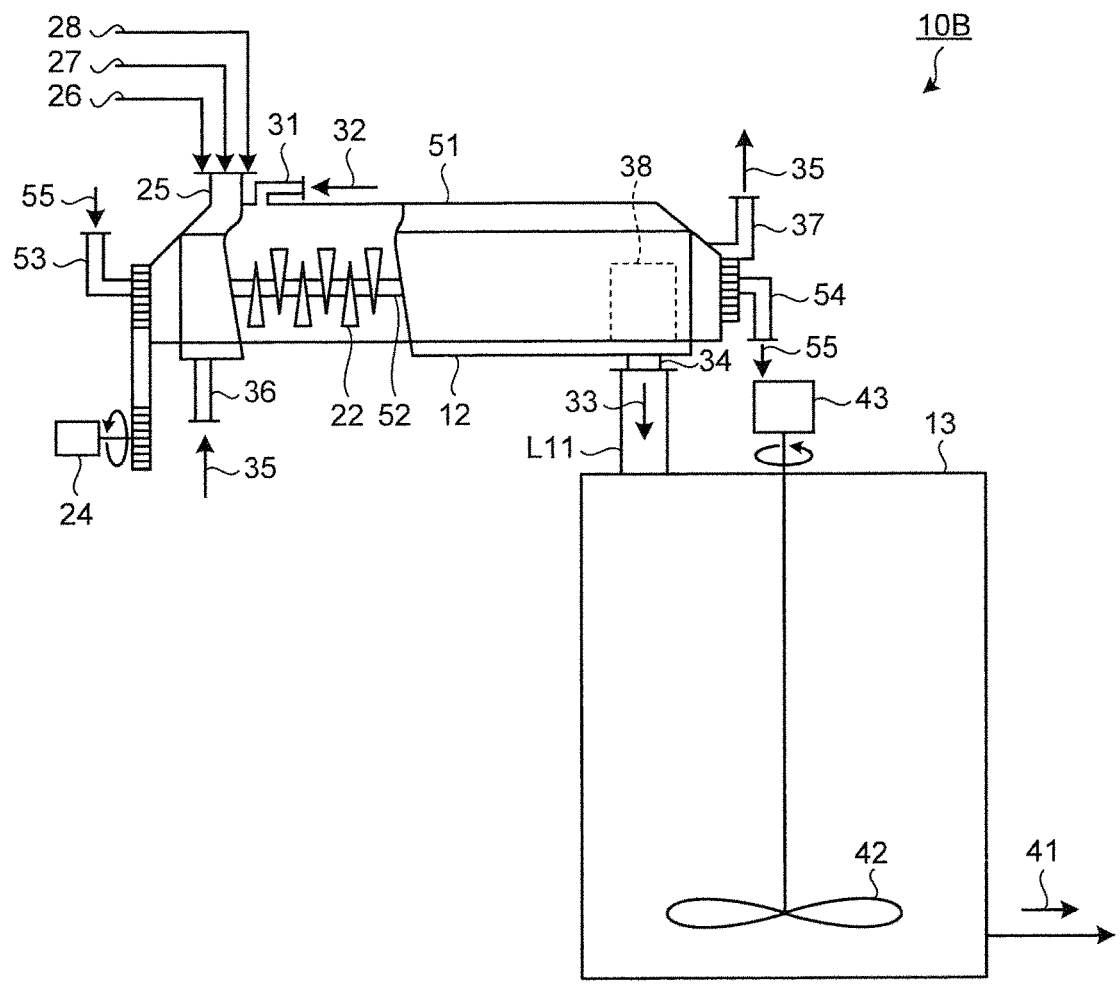
FIG. 8 is a schematic view illustrating the device that produces a sugar solution according to a second example.

FIG. 8 is a schematic view illustrating the sugar solution production device according to the second example. As illustrated in FIG. 8, a horizontal reaction tank 51 in a sugar solution production device 10B has a hollow stirring shaft 52, a warm water feed channel for a hollow rotator 53, and a warm water discharge channel for a hollow rotator 54.

The hollow stirring shaft 52 is a hollow body through which warm water 55 can flow.

The warm water 55 is fed into the hollow stirring shaft 52 through the warm water feed channel for a hollow rotator 53 and discharged to the warm water discharge channel for a hollow rotator 54 through the hollow stirring shaft 52.

Temperatures and water feed rates can be set to each of the warm waters 35 and 55 and they can be appropriately adjusted depending on the temperature in the horizontal reaction tank 51. The temperatures of the warm waters 35 and 55 may be the same as or different from each other. Particularly, the temperature of the warm waters 35 and 55 is preferably the same temperature from the viewpoint of economic efficiency.

When the cellulose-containing biomass 26 is pretreated, water or cold water having a temperature of 5° C. to 35° C. may be fed into the hollow stirring shaft 52 through the warm water feed channel for a hollow rotator 53 when the cellulose-containing biomass 26 is hot because the cellulose-containing biomass 26 is immediately after the pretreatment.

In the sugar solution production device 10B, in addition to controlling the temperature in the horizontal reaction tank 51 by the jacket 12, the temperature in the horizontal reaction tank 51 is controlled by flowing the warm water 55 through the hollow stirring shaft 52. This enables temperature adjustment in the horizontal reaction tank 51 in the sugar solution production device 10B to be easily carried out. Consequently, the temperature of the cellulose-containing biomass 26 can be adjusted more stably and thus the saccharified slurry 33 can be generated more stably.

Third Example

The sugar solution production device according to a third example will be described with reference to the drawings. The configuration of the sugar solution production device according to the third example is similar to the configuration of the sugar solution production device according to the first example as illustrated in FIG. 1 above and thus the same reference signs are assigned to the same members in the sugar solution production device according to the first example and the description of the same members is omitted.

Figure 9:
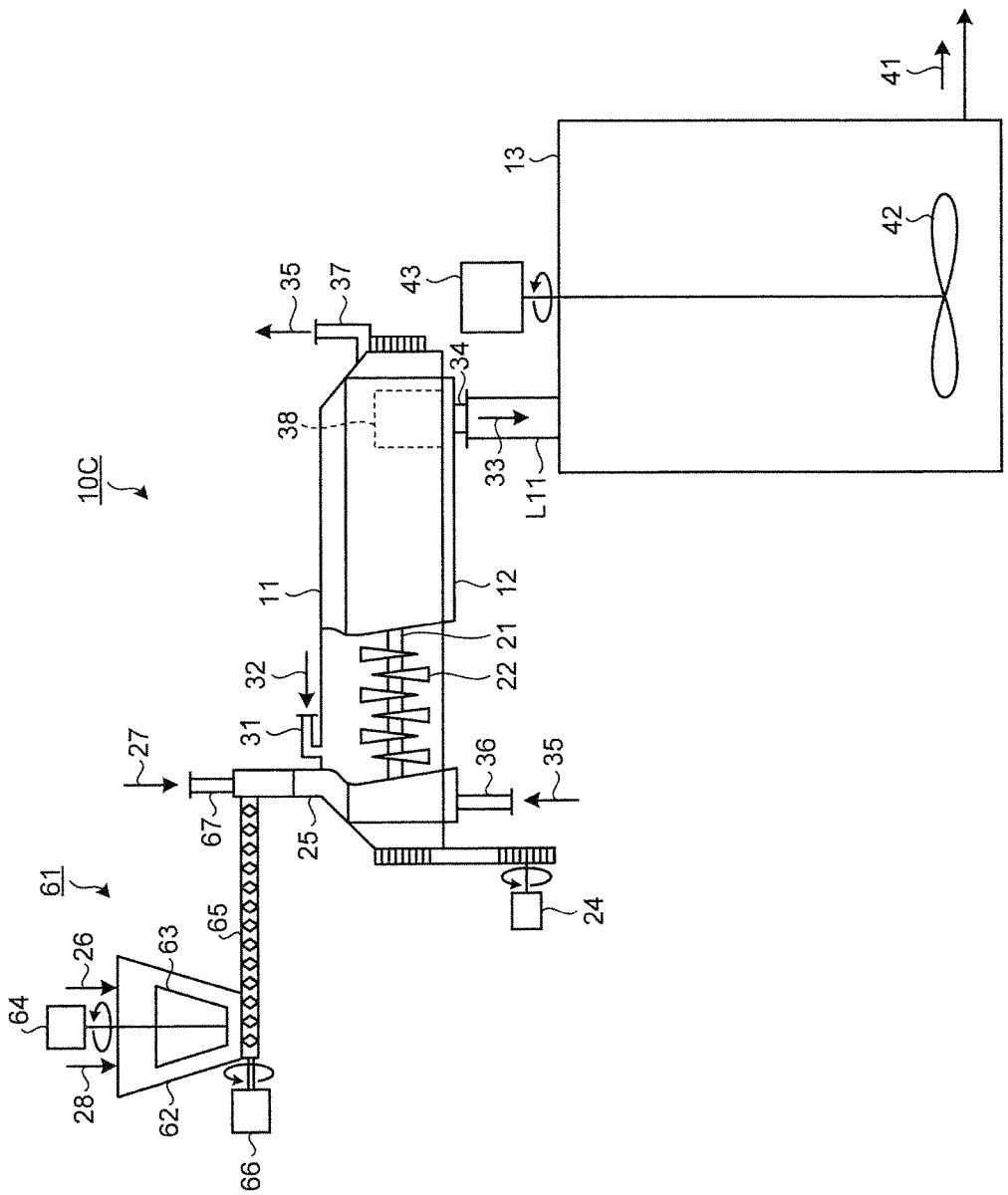
FIG. 9 is a schematic view illustrating the device that produces a sugar solution according to a third example.

FIG. 9 is a schematic view illustrating the sugar solution production device according to the third example. As illustrated in FIG. 9, a sugar solution production device 10C is further provided with a biomass feed unit (a biomass feed part) 61 in addition to the configuration of the sugar solution production device 10A.

The biomass feed unit 61 has a hopper 62, a feeder stirrer 63, a motor for a feeder stirrer (a feeder stirrer driving part) 64, a transfer unit 65, a motor for a transfer unit (a driving part for a transfer unit) 66, and a solid content adjustment water feed channel 67.

The hopper 62 is a tank for storing the cellulose-containing biomass 26 and the pH adjuster 28. The feeder stirrer 63 is a stirrer to mix the cellulose-containing biomass 26 and the pH adjuster 28 and prevents the cellulose-containing biomass 26 in the hopper 62 from forming a bridge. The motor for the feeder stirrer 64 is a motor that stirs the feeder stirrer 63. The transfer unit 65 is a unit for transferring the cellulose-containing biomass 26 and the pH adjuster 28. The transfer unit 65 is not particularly limiting. Examples of the transfer unit 65 may include a screw feeder or flight type conveyor using a chain.

The pH adjuster 28 and water 27 are fed into the hopper 62 and the solid content adjustment water feed channel 67, respectively, and each of them is separately mixed with the cellulose-containing biomass 26. However, this example is not limited to this configuration. The water 27 and the pH adjuster 28 may be fed into the hopper 62 or may be fed from the solid content adjustment water feed channel 67. Particularly, when the water and the pH adjuster 28 are fed to the hopper 62, excessive addition of the water 27 may cause clogging or accumulation of the biomass feed unit 61. Consequently, the pH adjuster 28 is preferably fed from the solid content adjustment water feed channel 67 together with the water 27.

Therefore, in the sugar solution production device 10C, two or more of the cellulose-containing biomass 26, the water 27, and the pH adjuster 28 are transferred by the biomass feed unit 61 and thus the cellulose-containing biomass 26, the water 27, and the pH adjuster 28 can be fed into the horizontal reaction tank 11 in stable feed rates. This allows the cellulose-containing biomass 26, the water 27, the pH adjuster 28, and the saccharification enzyme 32 to be quantitatively fed into the horizontal reaction tank 11 in the sugar solution production device 10C and thus slurry is stably formed from the cellulose-containing biomass 26 in the horizontal reaction tank 11. As a result, in the sugar solution production device 10C, a saccharification ratio of the cellulose-containing biomass 26, that is, the sugar concentration of the saccharified slurry 33 can be stabilized and thus the quality of the saccharified slurry 33 discharged from the saccharified slurry outlet 34 can be stabilized.

Fourth Example

The sugar solution production device according to a fourth example will be described with reference to the drawings. The configuration of the sugar solution production device according to this example is similar to the configuration of the sugar solution production device according to the first example as illustrated in FIG. 1 above and thus the same reference signs are assigned to the same members in the sugar solution production device according to the first example and the description of the same members is omitted.

Figure 10:
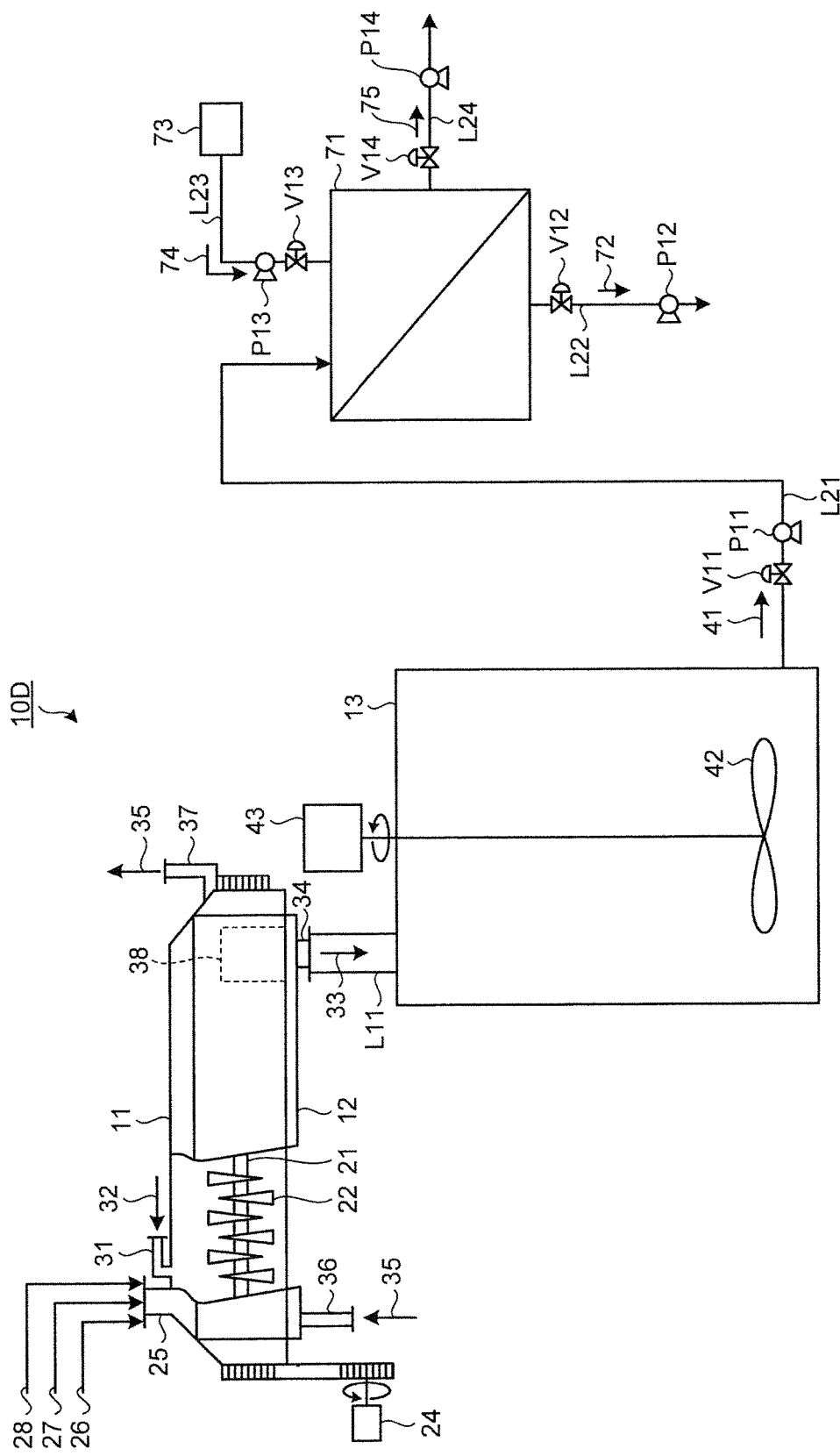
FIG. 10 is a schematic view illustrating the device that produces a sugar solution according to a fourth example.

FIG. 10 is a schematic view illustrating the sugar solution production device according to the fourth example. As illustrated in FIG. 10, a sugar solution production device 10D further has a solid-liquid separation unit 71, a saccharified liquid feed line L21, a sugar solution discharge line L22, a saccharification residue discharge line L24 and a warm water feed line L23 in addition to the configuration of the sugar solution production device 10A.

The solid-liquid separation unit 71 is a unit that separates the solid content from the saccharified liquid 41 to obtain the sugar solution 72. The solid-liquid separation unit 71 may be a unit that can separate the solid content from the saccharified liquid 41. Examples of the solid-liquid separation unit 71 may include centrifuge type units such as a screw decanter, a separation plate type centrifuge unit, a Sharples type centrifuge unit, and a vertical centrifuge unit; pressure filtration type units such as a filter press, a Pneumapress (registered trademark), a pressure filtration unit, a centrifugal filtration unit, a screw press, and a belt press; and suction filtration type units such as a belt filter, a pre-coat filter, a drum type filtration filter, and a vacuum filtration filter. Among them, particularly, the filter press of the pressure filtration type unit is preferably used as the solid-liquid separation unit 71 from the viewpoint that the unit has excellent recovery ratio of the sugar solution, can recover much sugar solution component by solid-liquid separation in one time and allows the clear filtrate to be easily obtained. The pressure filtration type or the suction type solid-liquid separation unit is preferably provided with an automatic washing function of a filter fabric and a filter from the viewpoint of long term operation performance. The number of washing times and the like are not particularly limiting.

The sugar solution 72 contains glucose derived from cellulose and xylose derived from hemicellulose. The mixing ratio of these sugars is different depending on the pretreatment method and the pretreatment conditions of the cellulose-containing biomass 26 and thus not particularly limiting. The sugar solution 72 is characterized in that the sugar solution 72 may contain organic acids such as formic acid and acetic acid generated at the time of decomposition of cellulose and hemicellulose, HMF and furfural generated from the sugars by the high temperature treatment, and the like, in addition to the substances described above. The sugar solution 72 also contains vanillin, guaiacol, coumaric acid, and ferulic acid derived from lignin, and the reactants thereof.

In the solid content, 50% or more of cellulose fraction and hemicellulose fraction each in the cellulose-containing biomass 26 is preferably hydrolyzed. The water content in the solid content is 40% or more and 80% or less. The water content of the solid content can be reduced to 55% or less when the solid-liquid separation unit 71 is the filter press.

When the solid-liquid separation unit 71 is the filter press, the saccharified liquid 41 is charged with pressure into a filtration chamber provided with a filter fabric by the pump and water is removed. Thereafter, a cake is preferably compressed with a diaphragm in the filter chamber to further remove water. When the cake formed by charging the saccharified liquid 41 with pressure into the filtration chamber provided with the filter fabric in the solid-liquid separation unit 71 and by removing water from the saccharified liquid 41 is compressed in a high pressure with the diaphragm, the compression pressure is not particularly limiting and is appropriately adjusted because the compression rate of the solid content is significantly affected by the pretreatment method of the biomass raw material, the biomass species, the enzyme saccharification efficiency and a bulk density of the biomass, and the like. The compressed pressure is, for example, 0.05 MPa or more and more preferably 0.5 MPa or more in view of the pretreatment method of the biomass raw material, the biomass species, the enzyme saccharification efficiency and the bulk density of the biomass, and the like. As the compression pressure becomes higher, the water content in the solid content can be lower and thus the yield of the sugar solution 72 is improved. Consequently, the compression pressure of 0.05 MPa or more enables the yield of the sugar solution 72 to be improved. When energy is recovered by burning the solid content by the compression, the combustion efficiency of the solid content is improved and thus higher energy can be obtained.

The saccharified liquid feed line L21 connects the vertical reaction tank 13 and the solid-liquid separation unit 71. The saccharified liquid 41 discharged from the vertical reaction tank 13 is fed into the solid-liquid separation unit 71 through the saccharified liquid feed line L21. The saccharified liquid feed line L21 is provided with a control valve V11 in the middle of the line and a saccharified liquid feed pump P11 located in the downstream side of the control valve V11. The feed amount of the saccharified liquid 41 is adjusted by the control valve V11 or the frequency of the saccharified liquid feed pump P11. The method of transferring the liquid is not necessarily a method using the pump. For example, method of transferring the liquid using compressed air may be employed. In other words, the saccharified liquid 41 may be transferred by using a pressure difference between the vertical reaction tank 13 and the solid-liquid separation unit 71. The saccharified liquid feed line L21 may be provided with a buffer tank, a feed tank, or the like.

The sugar solution discharge line L22 is connected to the permeation side of the solid-liquid separation unit 71. The sugar solution 72 obtained by separating the solid content from the saccharified liquid 41 in the solid-liquid separation unit 71 is discharged from the solid-liquid separation unit 71 through the sugar solution discharge line L22. The sugar solution discharge line L22 is provided with a control valve V12 in the middle of the line and a sugar solution feed pump P12 located in the rear flow side of the control valve V12. The feed amount of the sugar solution 72 is adjusted by the control valve V12 or the frequency of the sugar solution feed pump P12. The method of transferring the sugar solution 72 is not necessarily a method using the pump. The method may be the pressure transfer method described above or the sugar solution may be transferred by the free fall of the sugar solution caused by the gravity.

The warm water feed line L23 connects a warm water feed tank 73 and the non-permeation side of the solid-liquid separation unit 71. The warm water feed tank 73 is a tank for storing warm water 74 fed into the solid-liquid separation unit 71. The warm water 74 is fed into the solid-liquid separation unit 71 through the warm water feed line L23. The warm water feed line L23 is provided with a control valve V13 in the middle of the line and a warm water feed pump P13 located in the front stream side of the control valve V13. The feed amount of the warm water 74 is adjusted by the control valve V13 or the frequency of the warm water feed pump P13. The method of transferring the warm water 74 is not necessarily a method using the pump. The method may be the pressure transfer method described above.

Feed of the warm water 74 into the solid-liquid separation unit 71 through the warm water feed line L23 results in converting the solid content separated from the saccharified liquid 41 in the solid-liquid separation unit 71 into the sugar solution 72 by reacting the solid content with the saccharification enzyme 32 adsorbed to the solid content to carry out the hydrolysis using the warm water 74 that acts as a medium. This allows more sugar solution 72 and the saccharification enzyme 32 to be recovered. Consequently, the saccharification enzyme 32 to be charged can be reduced and can be efficiently used and the production amount of the sugar solution 72 can be increased.

The newly generated sugar solution 72 by the reaction with the saccharification enzyme 32 adsorbed to the solid content using the warm water 74 is discharged from the solid-liquid separation unit 71 through the sugar solution discharge line L22.

The added amount of the warm water 74 is not particularly limiting. The warm water 74 is preferably added so that the solid content concentration is 1% by mass to 20% by mass when the warm water 74 is reacted with the saccharification enzyme 32 adsorbed to the solid content to carry out the hydrolysis. The solid content concentration of more 20% by mass or less than 1% by mass is inefficient from the viewpoint of the production amount of the sugar solution 72 and the recovery ratio of the saccharification enzyme 32 and thus is not preferable.

The temperature of the warm water 74 is preferably 30° C. to 60° C., more preferably 40° C. to 55° C., and further preferably around 50° C.

The time of reacting the warm water 74 with the saccharification enzyme 32 adsorbed to the solid content to carry out the hydrolysis is preferably 1 minute to 180 minutes. The reaction time of less than 1 minute results in low recovery efficiency of the saccharification enzyme 32 adsorbed to the solid content whereas the reaction time of more than 180 minutes results in not improving the recovery efficiency of the saccharification enzyme 32 adsorbed to the solid content and thus is inefficient.

The pH of the warm water 74 is preferably 6.0 to 8.0 and more preferably about 5.0. The pH of less than 6.0 results in a low recovery ratio of the saccharification enzyme 32 adsorbed to the solid content whereas the pH of more than 8.0 results in deactivation of the saccharification enzyme 32 and thus is not preferable. Consequently, the pH of 6.0 to 8.0 results in reducing the deactivation of the saccharification enzyme 32 as low as possible and improving the recovery efficiency of the saccharification enzyme 32.

The saccharification enzyme 32 recovered in the solid-liquid separation unit 71 may be reused. From the viewpoint of reduction in the used amount of the saccharification enzyme 32, particularly reduction in the used amount of an unused saccharification enzyme, both of the recovered saccharification enzyme 32 and the unused saccharification enzyme are preferably mixed to be used. The recovery efficiency of the saccharification enzyme 32 can also be increased by adding into the vertical reaction tank 13 an adsorption inhibitor for blocking the site of the saccharification enzyme 32 that is adsorbed and undetached from the cellulose-containing biomass 26 due to the adsorption to improve the recovery efficiency of the saccharification enzyme 32, and thereafter adding the unused saccharification enzyme into the vertical reaction tank 13.

The feed period of the warm water 74 into the solid-liquid separation unit 71 is not particularly limiting. From the viewpoint of the efficient solid-liquid separation of the saccharified liquid 41, for example, the warm water 74 is more preferably fed after further removal of water from the cake generated from the water-removed saccharified liquid 41 by the compression using the diaphragm when the solid-liquid separation unit 71 is the filter press. In other words, the feed of the warm water 74 into the solid-liquid separation unit 71 after the compression of the saccharified liquid 41 results in reduction in the used amount of the warm water 74 and improvement of permeation efficiency because this feed method reduces the volume of the solid content and the water content.

The saccharification residue discharge line L24 is connected to the non-permeation side of the solid-liquid separation unit 71. The solid content remaining after feeding the warm water 74 into the solid-liquid separation unit 71 is discharged as a saccharification residue 75 from the solid-liquid separation unit 71 through the saccharification residue discharge line L24. The saccharification residue discharge line L24 is provided with a control valve V14 in the middle of the line and a pump for saccharification residue discharge P14 located in the downstream side of the control valve V14. The discharged amount of the saccharification residue 75 is adjusted by the control valve V14 or the frequency of the pump for saccharification residue discharge P14. The saccharification residue 75 is often a solid-like product. Consequently, a method of discharging the saccharification residue 75 is preferably a belt conveyer or the like suitable for transferring a solid content, rather than a pipe or a pump. Particularly, when the filter press or Pneumapress (registered trademark) is used as the solid-liquid separation unit 71, the saccharification residue 75 is preferably transferred by the belt conveyer or the like after the saccharification residue 75 is discharged by transferring the filter fabric, moving the filter fabric, or transferring a scraper onto the filter fabric.

The saccharified liquid 41 contains the sugar solution 72 and the solid content. The solid content contains polysaccharide components such as undecomposed cellulose or hemicellulose and components such as lignin that cannot be decomposed by the saccharification enzyme 32. The solid content is in a state that a relatively large amount of the saccharification enzyme 32 is adsorbed. Consequently, the solid-liquid separation unit 71 separates the saccharified liquid 41 into the sugar solution 72 and the solid content to obtain the sugar solution 72 and recover the solid content. The solid content separated from the saccharified liquid 41 in the solid-liquid separation unit 71 contains the polysaccharide components and the saccharification enzyme 32. The polysaccharide components and the saccharification enzyme 32 contained in the solid content of the saccharified liquid 41 are contained in the warm water 74 fed into the solid-liquid separation unit 71 and are used to generate the sugar solution 72. The residue of the solid content not used to generate the sugar solution 72 is discharged as the saccharification residue 75 from the solid-liquid separation unit 71 through the saccharification residue discharge line L24.

As described above, the sugar solution production device 10D is provided with the solid-liquid separation unit 71, collects the solid content in the non-permeation side of the solid-liquid separation unit 71, and obtains the sugar solution 72 as a liquid component in the permeation side. In the sugar solution production device 10D, the sugar solution 72 is generated by adding the warm water 74 into the solid-liquid separation unit 71 and by reacting the warm water 74 with the saccharification enzyme 32 adsorbed to the solid content in the solid-liquid separation unit 71 to carry out the hydrolysis. This allows more sugar solution 72 to be recovered and the added saccharification enzyme 32 to be used. Consequently, the newly charged saccharification enzyme 32 can be efficiently used and the sugar solution 72 can be efficiently produced in a low cost. As a result, the sugar solution production device 10D can further improve the saccharification efficiency than the first to third examples and thus the saccharification reaction of the cellulose-containing biomass 26 can be carried out in a short period of time.

In this example, the warm water 74 is discharged from the sugar solution discharge line L22 after the warm water 74 is fed to the solid-liquid separation unit 71. However, this example is not limited to this configuration. The warm water 74 may be reused by providing a warm water return line in the permeation side of the solid-liquid separation unit 71, feeding the warm water 74 to the warm water feed tank 73, and circulating the warm water 74. The warm water 74 used in the solid-liquid separation unit 71 can be transferred to the warm water feed tank 73 by providing the warm water return line and thus the used amount of the warm water 74 can be reduced by circulating the warm water 74 used in the solid-liquid separation unit 71 through the warm water return line to reuse the warm water 74.

In this case, the total volume of the used circulating warm water 74 may be finally discharged as the sugar solution 72 from the sugar solution discharge line L22 through the solid content in the solid-liquid separation unit 71 or the warm water 74 was circulated between the solid-liquid separation unit 71 and the warm water feed tank 73 and thereafter may be discharged as the sugar solution 72 from a line different from the sugar solution discharge line L22.

The sugar solution production device 10D is provided with one vertical reaction tank 13. However, this example is not limited to this configuration. The solid-liquid separation may be carried out by serially providing the vertical reaction tanks 13 and carrying out the continuous saccharification reaction. FIG. 11 is a view illustrating another example of the configuration of the sugar solution production device 10E. As illustrated in FIG. 11, the sugar solution production device 10E is serially provided with a vertical reaction tank 13-1 and a vertical reaction tank 13-2. The vertical reaction tank 13-1 and the vertical reaction tank 13-2 are connected by a saccharified liquid feed line L21-1 and the vertical reaction tank 13-2 and the solid-liquid separation unit 71 connect by a saccharified liquid feed line L21-2. A saccharified liquid 41A discharged from the vertical reaction tank 13-1 is fed into the vertical reaction tank 13-2 through the saccharified liquid feed line L21-1. The saccharified liquid feed line L21-1 is provided with a control valve V11-1 in the middle of the line and a saccharified liquid feed pump P11-1 located in the downstream side of the control valve V11-1. A saccharified liquid 41B discharged from the vertical reaction tank 13-2 is fed to the solid-liquid separation unit 71 through the saccharified liquid feed line L21-2. The saccharified liquid feed line L21-2 is provided with a control valve V11-2 in the middle of the line and a saccharified liquid feed pump P11-2 located in the downstream side of the control valve V11-2.

Similar to the sugar solution production device 10D, the sugar solution production device 10E is also provided with the solid-liquid separation unit 71 and the saccharification residue discharge line L24. Even if a plurality of vertical reaction tanks (in this example, two tanks of the vertical reaction tank 13-1 and the vertical reaction tank 13-2) are provided, the saccharified slurry 33 can be continuously treated while retaining the saccharification efficiency per vertical reaction tank in each of the vertical reaction tanks 13-1 and 13-2 by promoting the saccharification reaction of the saccharified slurry 33 in each of the vertical reaction tanks 13-1 and 13-2. As a result, similar to the sugar solution production device 10D, the sugar solution production device 10E can further improve the saccharification efficiency of the cellulose-containing biomass 26 and can shorten the saccharification reaction of the cellulose-containing biomass 26.

Each of the saccharified liquid feed line L21, the warm water feed line L23, and saccharification residue discharge line L24 is separately connected to the solid-liquid separation unit 71. However, this example is not limited to this configuration. At least one or more of the saccharified liquid feed line L21, the warm water feed line L23, and saccharification residue discharge line L24 may be shared. When the solid-liquid separation unit 71 is, for example, a filter press, the number of inlets and outlets for the liquid may be limited due to the configuration of the filter press. By sharing at least one or more of the saccharified liquid feed line L21, the warm water feed line L23, and saccharification residue discharge line L24, the solid-liquid separation of the saccharified liquid 41 can be efficiently carried out depending on the unit configuration used as the solid-liquid separation unit 71 even when the solid-liquid separation unit 71 is a tank in which the number of inlets and outlets for the liquid may be limited such as the filter press.

The sugar solution 72 is generated by extracting the sugar solution 72 by feeding the saccharified liquid 41 into the solid-liquid separation unit 71 and, thereafter, feeding the warm water 74 into the solid-liquid separation unit 71 to react the warm water 74 with the saccharification enzyme 32 adsorbed to the solid content in the solid-liquid separation unit 71. After the sugar content is reduced from the solid content, the solid content was discharged as the saccharification residue 75. The order of the feed of the saccharified liquid 41 and warm water 74 into the solid-liquid separation unit 71 and the extraction of the sugar solution 72 are not particularly limiting and can be appropriately adjusted.

An example that the sugar solution production device 10A according to the first example is used as the sugar solution production device is described. However, this example is not limited to this configuration, and the sugar solution production devices 10B and 10C according to the second and the third examples, respectively, may be used.

WORKING EXAMPLES

Example 1: Preparation and Analysis of Saccharified Liquid

A. Preparation of Pretreated Cellulose-Containing Biomass
1. Blasting Treatment of Cellulose-Based Biomass Rice straw was used as the cellulose-containing biomass. First, 100 kg of rice straw was grinded with the rotary cutter mill Type RCM-400 (manufactured by Nara Machinery Co. Ltd.) in a state of a screen mesh diameter of 8 mm at a rotation speed of 420 rpm. Subsequently, water vapor blasting treatment was carried out for 2 kg of the grind treated rice straw using a blasting apparatus (reaction container 30 L, manufactured by Nippon Dennetsu Co., Ltd.). At this time, the pressure was 2.5 MPa and the treating time was 3 minutes.

2. Ammonia Treatment of Cellulose-Based Biomass

Rice straw was used as the cellulose-containing biomass. First, 1 kg of rice straw was grinded with the rotary cutter mill Type RCM-400 (manufactured by Nara Machinery Co. Ltd.) in a state of a screen mesh diameter of 8 mm at a rotation speed of 420 rpm. Subsequently, by using an autoclave apparatus (reaction container 3 L, manufactured by NITTO KOUATSU CO., LTD.), 500 g of the grind treated rice straw was placed in the autoclave and pure ammonia gas was introduced into the autoclave to carry out the ammonia treatment under the conditions of 120° C. for 10 minutes with stirring. This operation was repeated multiple times to obtain about 20 kg of pretreated biomass.

B. Preparation of Saccharified Liquid

Each 2 kg of the pretreated biomass obtained in the processes of "A. Preparation of pretreated cellulose-containing biomass" in a dry mass was separately collected and saccharification reaction was carried out for each sample. The saccharification reaction was continuously carried out using Boono Dryer manufactured by Nara Machinery Co. Ltd. (hold volume: about 30 L) as the horizontal reaction tank. The saccharification reaction was carried out by feeding warm water at 50° C. to a jacket only. The reaction time was determined to be 30 minutes in accordance with the hold amount of 30 L. The pretreated biomass, a pH adjuster (sulfuric acid or aqueous sodium hydroxide solution), an enzyme solution (Accellerase (registered trademark) DUET, cellerase, manufactured by Danisco Japan Ltd.), and water were continuously charged. Each additive was added as follows. The pH adjuster was added so that the pH was 4.8. The enzyme solution was added so that 200 mL of the enzyme solution was added relative to 1 kg dry mass of the pretreated biomass. Water was added in amounts so that solid content concentrations including the pH adjuster and the enzyme solution were 10 wt %, 15 wt %, 20 wt %, and 30 wt %. Then, the saccharification reaction was carried out. Thereafter, 20 L of the discharged saccharified slurry was separately collected and the saccharification reaction was carried out in a jacket-type reaction tank having a whole volume of 25 L as the vertical reaction tank. The saccharification reaction was terminated 6 hours and 24 hours after the starting time of the addition of the initial pretreated biomass into the Boono Dryer as the horizontal reaction tank.

C. Analysis of Sugar Concentration

1. Analysis Method of Sugars

Sugar concentrations (g/L) of the saccharified liquids obtained above were measured. The sugar concentrations in the obtained saccharified liquids were quantitatively measured in comparison with the standard samples under the following High Performance Liquid Chromatography (HPLC) conditions. The results are listed in Table 1.

Column: Luna $NH_2$ (manufactured by Phenomenex Inc.)
Mobile phase: Ultrapure water:acetonitrile=25:75
Flow rate: 0.6 mL/min
Reaction liquid: None
Detection method: RI (differential refractive index)
Temperature: 30° C.

2. Analysis Method of Solid Content Concentration

The solid content concentrations of the saccharified liquids obtained above were measured. The solid content concentration was determined as follows by using an infrared moisture meter (manufactured by Kett Electric Laboratory). A sample containing the saccharified liquid was retained at a temperature of 120° C. A water content that is a value obtained from the difference between a stabilized value after evaporation and an initial value was measured and the value calculated by subtracting the water content from 100 wt % was determined as the solid content concentration. The results are listed in Table 1.

TABLE 1

| Solid content concentration | Type of sugar | Blasting treatment [g/L] | | Ammonia treatment [g/L] | |
|---|---|---|---|---|---|
| | | After 6 hours | After 24 hours | After 6 hours | After 24 hours |
| 10 wt % | Glucose | 26 | 36 | 18 | 27 |
| | Xylose | 7 | 7 | 16 | 18 |
| 15 wt % | Glucose | 34 | 57 | 24 | 42 |
| | Xylose | 8 | 12 | 24 | 27 |
| 20 wt % | Glucose | 44 | 72 | 31 | 55 |
| | Xylose | 12 | 14 | 30 | 36 |
| 30 wt % | Glucose | 64 | 98 | 46 | 72 |
| | Xylose | 16 | 21 | 44 | 49 |

From the results in Table 1, we ascertained that the saccharification reaction efficiency was improved by first saccharifying the pretreated biomass in the horizontal reaction tank and thereafter carrying out the saccharification reaction in the vertical reaction tank. It was also ascertained that the saccharification reaction in a high concentration was able to be carried out in the vertical reaction tank. Consequently, the scale of the saccharification reaction tank can be reduced. This can reduce the facility cost.

Example 2: Heat Retention of Stirring Shaft

In a similar method to Example 1, the saccharification reaction of the pretreated biomass obtained in "A. Preparation of pretreated cellulose-containing biomass" was continuously carried out by flowing warm water at 50° C. not only in the jacket but also in the stirring shaft in the Boono Dryer as the horizontal reaction tank. The saccharification reaction was terminated 6 hours and 24 hours after the starting time of the addition of the initial pretreated biomass into the Boono Dryer as the horizontal reaction tank and the sugar concentrations were measured. The results are listed in Table 2.

TABLE 2

| Solid content concentration | Type of sugar | Blasting treatment [g/L] | | Ammonia treatment [g/L] | |
|---|---|---|---|---|---|
| | | After 6 hours | After 24 hours | After 6 hours | After 24 hours |
| 10 wt % | Glucose | 26 | 36 | 18 | 27 |
| | Xylose | 7 | 7 | 16 | 18 |
| 15 wt % | Glucose | 36 | 57 | 32 | 42 |
| | Xylose | 9 | 12 | 26 | 27 |
| 20 wt % | Glucose | 50 | 74 | 35 | 56 |
| | Xylose | 14 | 15 | 30 | 36 |
| 30 wt % | Glucose | 72 | 99 | 52 | 74 |
| | Xylose | 22 | 21 | 46 | 50 |

From the results in Table 2, we ascertained that sugar concentration was increased and that the saccharification reaction can be further efficiently carried out by flowing warm water in the stirrer of the horizontal reaction tank.

Example 3: Concomitant Use of Filtration Type Solid-Liquid Separation Unit

The saccharification reaction of the saccharified liquid obtained in Example 2 was terminated after 6 hours and further solid-liquid separation was carried out using a filter press (manufactured by Daiki Ataka Engineering Co., Ltd.) as the filtration type solid-liquid separation unit. After the solid-liquid separation, 5 L of warm water at 50° C. was fed to the filter press and compression was performed. The total amount and the concentration of the saccharified liquid and the obtained sugar solution were measured by using "1. Analysis method of sugars" described above. The results are listed in Table 3.

TABLE 3

| | | Blasting treatment | | | | Ammonia treatment | | | |
| | | Without filtration unit | | With filtration unit | | Without filtration unit | | With filtration unit | |
| Solid content concentration | Type of sugar | Sugar concentration [g/L] | Sugar yield [g] | Sugar concentration [g/L] | Sugar yield [g] | Sugar concentration [g/L] | Sugar yield [g] | Sugar concentration [g/L] | Sugar yield [g] |
|---|---|---|---|---|---|---|---|---|---|
| 15 wt % | Glucose | 36 | 684 | 30 | 720 | 32 | 608 | 28 | 672 |
| | Xylose | 9 | 171 | 7 | 168 | 26 | 494 | 22 | 528 |
| 20 wt % | Glucose | 50 | 950 | 43 | 1032 | 35 | 665 | 32 | 768 |
| | Xylose | 14 | 266 | 12 | 288 | 30 | 570 | 25 | 600 |
| 30 wt % | Glucose | 72 | 1368 | 69 | 1656 | 52 | 988 | 50 | 1200 |
| | Xylose | 22 | 418 | 18 | 432 | 46 | 874 | 38 | 912 |

From the results in Table 3, we ascertained that the saccharification reaction was promoted in a filtration chamber of the filter press by filtrating the obtained saccharified liquid with the filter press and feeding the warm water at 50° C. and the yield of the mass of the obtained sugar was increased compared with the saccharified liquid. We also ascertained that, as the yield of the sugar, the sugar concentration obtained by the saccharification reaction for about 6 hours was almost equal to the sugar concentration obtained after saccharification for 24 hours. This indicates that the facility cost can be reduced. The mass of the sugar was calculated based on a liquid amount of 19 L and a liquid amount after washing of 24 L, assuming that an undecomposed biomass was 1 kg in the case of no filtration unit. As a result, we ascertained that the sugar yield was also increased by carrying out the warm water washing of the saccharification residue.

Comparative Example 1

Similar to Examples 1 to 3, each 2 kg of the pretreated biomass obtained in the process "A. Preparation of pretreated cellulose-containing biomass" described above in a dry mass was separately collected and saccharification reaction was carried out using a jacket type reaction tank having a whole volume of 25 L as the vertical reaction tank. As the saccharification conditions, sodium hydroxide or sulfuric acid was used for the blasted biomass or the ammonia treated biomass, respectively, to adjust the pH to 4.8 and thereafter 400 mL of Accellerase DUET (manufactured by Danisco Japan Ltd) was added. The saccharification reaction was carried out by adding water so that the solid content concentration was 10 wt %, 15 wt %, and 20 wt %, while retaining the temperature of the jacket at 50° C. by using warm water. The saccharification reaction was terminated 6 hours and 24 hours after the starting time of the addition of the initial pretreated biomass and the sugar concentrations were measured. The results are listed in Table 4.

TABLE 4

| Solid content concentration | Type of sugar | Blasting treatment [g/L] | | Ammonia treatment [g/L] | |
| | | After 6 hours | After 24 hours | After 6 hours | After 24 hours |
|---|---|---|---|---|---|
| 10 wt % | Glucose | 24 | 34 | 17 | 27 |
| | Xylose | 6 | 7 | 16 | 18 |
| 15 wt % | Glucose | 18 | 46 | 12 | 36 |
| | Xylose | 7 | 10 | 10 | 22 |
| 20 wt % | Glucose | 18 | 50 | 14 | 40 |
| | Xylose | 7 | 12 | 14 | 28 |

From the results in Table 4, we ascertained that, in any of the solid content concentrations, the sugar concentrations were lower than the sugar concentrations in Examples 1. The viscosities were too high to rotate the stirrer in the initial stage of the reaction in the case of the solid content concentrations of 15 wt % and 20 wt %. However, the viscosities were lowered after 50 minutes for the solid content concentration of 15 wt % and after 150 minutes for the solid content concentration of 20 wt % and then the stirrer was able to be rotated.

Comparative Example 2

Similar to Examples 1 to 3, each 2 kg of the pretreated biomass obtained in the process "A. Preparation of pretreated cellulose-containing biomass" described above in a dry mass was separately collected and the saccharification reaction was carried out for each pretreated biomass. The saccharification reaction was continuously carried out using Boono Dryer manufactured by Nara Machinery Co., Ltd. (hold volume: about 30 L) as the horizontal reaction tank as the saccharification tank. The saccharification reaction was carried out by feeding warm water at 50° C. to the jacket only. The reaction time was determined to be 24 hours in accordance with the hold amount of 30 L. The pretreated biomass, the pH adjuster (sulfuric acid or aqueous sodium hydroxide solution), the enzyme solution (Accellerase DUET, manufactured by Danisco Japan Ltd), and water were continuously charged. The reaction was operated for 3 days in total. Each addition rate was as follows. The pH adjuster was added so that the pH of the saccharified liquid was 4.8. The enzyme solution was added so that 200 mL of the enzyme solution was added relative to 1 kg dry mass of the pretreated biomass. Water was added in amounts so that solid content concentrations including the pH adjuster and the enzyme solution were 10 wt %, 15 wt %, 20 wt %, and 30 wt %. Then, the saccharification reaction was carried out.

The stable sugar solutions were not obtained because the solid content in each obtained solution was accumulated at the bottom of Boono Dryer. Finally, the stirrer was not able to be rotated due to the solid content accumulated at the bottom. As described above, the saccharification cannot be continuously treated by using the horizontal reaction tank only. Consequently, we ascertained that the concomitant use of the horizontal reaction tank and the vertical reaction tank was able to further improve the saccharification efficiency in Example 1.

Comparative Example 3: No Heat Retention of Horizontal Reaction Tank

Similar to Examples 1 to 3, each 2 kg of the pretreated biomass obtained in the process of "A. Preparation of pretreated cellulose-containing biomass" in a dry mass was separately collected and the saccharification reaction was carried out for each pretreated biomass. The saccharification reaction was continuously carried out using Boono Dryer manufactured by Nara Machinery Co., Ltd. (hold volume: about 30 L) as the horizontal reaction tank as the saccharification tank. Warm water did not flow through the jacket and the stirring shaft and the saccharification reaction was carried out without temperature control. The outside temperature was 25° C. The reaction time was determined to be 30 minutes in accordance with the hold amount of 30 L. The pretreated biomass, a pH adjuster (sulfuric acid or aqueous sodium hydroxide solution), an enzyme solution (Accellerase (registered trademark) DUET), and water were continuously charged. Addition rates were as follows. The pH adjuster was added so that the pH was 4.8. The enzyme solution was added so that 200 mL of the enzyme solution was added relative to the 1 kg dry mass of the pretreated biomass. Water was added in amounts so that solid content concentrations including the pH adjuster and the enzyme solution were 10 wt %, 15 wt %, 20 wt %, and 30 wt %. Then, the saccharification reaction was carried out. Thereafter, 20 L of the discharged saccharified slurry was separately collected and the saccharification reaction was carried out in a jacket-type reaction tank having a whole volume of 25 L as the vertical reaction tank. The saccharification reaction was terminated 6 hours and 24 hours after the starting time of the addition of the initial pretreated biomass into the Boono Dryer as the horizontal reaction tank. The sugar concentrations were measured. The results are listed in Table 5.

TABLE 5

| Solid content concentration | Type of sugar | Blasting treatment [g/L] After 6 hours | Blasting treatment [g/L] After 24 hours | Ammonia treatment [g/L] After 6 hours | Ammonia treatment [g/L] After 24 hours |
| --- | --- | --- | --- | --- | --- |
| 10 wt % | Glucose | 21 | 32 | 16 | 25 |
|  | Xylose | 6 | 7 | 12 | 18 |
| 15 wt % | Glucose | 32 | 51 | 29 | 38 |
|  | Xylose | 6 | 11 | 21 | 25 |
| 20 wt % | Glucose | 30 | 61 | 21 | 42 |
|  | Xylose | 10 | 13 | 20 | 25 |
| 30 wt % | Glucose | 40 | 70 | 30 | 58 |
|  | Xylose | 14 | 16 | 29 | 32 |

From the results in Table 5, we ascertained that, in any of the solid content concentrations, the sugar concentrations were lower than the sugar concentrations in Examples 1 and 2. In the solid content concentration of 20 wt % and 30 wt %, a phenomenon that the stirrer was not rotatable for 1 hour and 2 hours, respectively, due to excessively high viscosity occurred at the time of saccharification in the vertical reaction tank. In this way, we ascertained from the comparison with Examples 1 and 2 that the temperature control of the horizontal reaction tank was extremely important for the saccharification reaction.

INDUSTRIAL APPLICABILITY

The device that produces a sugar solution and the method of producing a sugar solution can be suitably employed to efficiently produce the sugar solution having a high concentration.

The invention claimed is:

1. A device that produces a sugar solution from cellulose-containing biomass comprising:
   a horizontal reaction tank that includes a stirring shaft provided along a horizontal direction in the horizontal reaction tank and a stirring blade provided to the stirring shaft, the horizontal reaction tank being configured to obtain a saccharified slurry by reacting the cellulose-containing biomass with a saccharification enzyme by stirring the cellulose-containing biomass and the saccharification enzyme;
   a vertical reaction tank configured to obtain a saccharified liquid by saccharifying the saccharified slurry;
   a saccharified slurry feed line that connects the horizontal reaction tank and the vertical reaction tank; and
   a warming part provided around the horizontal reaction tank or on a wall surface of the horizontal reaction tank and heats the horizontal reaction tank,
   wherein the horizontal reaction tank comprises:
   a biomass inlet located at one side of the horizontal reaction tank and feeds the cellulose-containing biomass;
   a saccharified slurry outlet located at another side of the horizontal reaction tank opposite to the biomass inlet and discharges the saccharified slurry,
   a stemming part located at the saccharified slurry outlet and stems stream of the saccharified slurry,
   the stemming part is a plate-shaped member contiguous with a bottom wall of the horizontal reaction tank and extending from the bottom wall toward a top wall of the horizontal reaction tank to form an opening between a top end of the plate-shaped member and the top wall such that the opening communicates with the saccharified slurry outlet, and
   a height of the stemming part is adjustable to provide continuous discharge of the saccharified slurry.

2. The device according to claim 1, wherein the stirring shaft is heated.

3. The device according to claim 1, wherein at least one of the stirring shaft and the warming part is a hollow body through which a heat transfer medium is capable of flowing.

4. The device according to claim 3, wherein a temperature of the heat transfer medium is 40° C. to 60° C.

5. The device according to claim 1, further comprising a biomass feed part located at a front stream side of the biomass inlet of the horizontal reaction tank and feeds the cellulose-containing biomass.

6. The device according to claim 1, further comprising:
   a saccharified liquid feed line that discharges the saccharified liquid from the vertical reaction tank; and
   a solid-liquid separation unit configured to obtain the sugar solution by separating a solid content from the saccharified liquid.

7. The device according to claim 6, further comprising a warm water feed line connected to the solid-liquid separation unit and feeds warm water into the solid-liquid separation unit.

8. The device according to claim 1, wherein
   the horizontal reaction tank is provided with a plurality of such stirring shafts, and
   each of the stirring shafts is provided with a plurality of stirring blades.

9. The device according to claim 1, wherein the stirring blade has a cut-away part.

10. The device according to claim 1, wherein the vertical reaction tank comprises a second enzyme feed channel that feeds a saccharification enzyme into the vertical reaction tank.

11. The device according to claim 10, wherein a saccharification enzyme fed into the horizontal reaction tank and a saccharification enzyme fed from the second enzyme feed channel are of different types.

12. The device according to claim 1, wherein a saccharification reaction of the cellulose-containing biomass with the saccharification enzyme in the horizontal reaction tank is carried out in an amount of dry mass of thermochemically treated cellulose-containing biomass of 15% by mass to 50% by mass relative to a whole mass of the saccharified slurry.

13. The device according to claim 12, wherein the thermochemical treatment is selected from the group consisting of ammonia treatment, hydrothermal treatment, blasting treatment, alkali treatment and dilute sulfuric acid treatment.

14. A method of producing a sugar solution from cellulose-containing biomass with a device that produces a sugar solution, the device comprising:
- a horizontal reaction tank that includes a stirring shaft provided along a horizontal direction in the horizontal reaction tank and a stirring blade provided to the stirring shaft, the horizontal reaction tank being configured to obtain a saccharified slurry by reacting the cellulose-containing biomass with a saccharification enzyme by stirring the cellulose-containing biomass and the saccharification enzyme;
- a vertical reaction tank configured to obtain a saccharified liquid by saccharifying the saccharified slurry;
- a saccharified slurry feed line that connects the horizontal reaction tank and the vertical reaction tank; and
- a warming part provided around the horizontal reaction tank or on a wall surface of the horizontal reaction tank and heats the horizontal reaction tank, the method comprising reacting the cellulose-containing biomass with the saccharification enzyme with stirring and with heat to obtain a saccharified slurry liquid, wherein the horizontal reaction tank comprises:
- a biomass inlet located at one side of the horizontal reaction tank and feeds the cellulose-containing biomass;
- a saccharified slurry outlet located at another side of the horizontal reaction tank opposite to the biomass inlet and discharges the saccharified slurry,
- a stemming part located at the saccharified slurry outlet and stems stream of the saccharified slurry, and
- the stemming part is a plate-shaped member contiguous with a bottom wall of the horizontal reaction tank and extending from the bottom wall toward a top wall of the horizontal reaction tank to form an opening between a top end of the plate-shaped member and the top wall such that the opening communicates with the saccharified slurry outlet.

15. The device according to claim 1, wherein the saccharified slurry outlet is surrounded by the stemming part and the wall surface of the horizontal reaction tank.

* * * * *